(12) United States Patent
McKernan

(10) Patent No.: US 12,391,999 B2
(45) Date of Patent: *Aug. 19, 2025

(54) METHODS AND KITS FOR CLASSIFYING CANNABINOID PRODUCTION IN CANNABIS PLANTS

(71) Applicant: MEDICINAL GENOMICS CORPORATION, Beverly, MA (US)

(72) Inventor: Kevin McKernan, Marblehead, MA (US)

(73) Assignee: MEDICINAL GENOMICS CORPORATION, Beverly, MA (US)

( * ) Notice: Subject to any disclaimer, the term of this patent is extended or adjusted under 35 U.S.C. 154(b) by 1102 days.

This patent is subject to a terminal disclaimer.

(21) Appl. No.: 17/346,709

(22) Filed: Jun. 14, 2021

(65) Prior Publication Data

US 2022/0017974 A1 Jan. 20, 2022

Related U.S. Application Data

(62) Division of application No. 16/221,171, filed on Dec. 14, 2018, now Pat. No. 11,035,010.

(60) Provisional application No. 62/598,967, filed on Dec. 14, 2017.

(51) Int. Cl.
*C12Q 1/6895* (2018.01)
*C12N 9/02* (2006.01)

(52) U.S. Cl.
CPC ......... *C12Q 1/6895* (2013.01); *C12N 9/0004* (2013.01); *C12Y 121/03007* (2015.07); *C12Y 121/03008* (2015.07); *C12Q 2600/13* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| 5,102,784 | A | 4/1992 | George, Jr. |
| 6,410,278 | B1 | 6/2002 | Notomi et al. |
| 2012/0157326 | A1 | 6/2012 | Tisi et al. |
| 2014/0057251 | A1 | 2/2014 | McKernan |
| 2016/0177404 | A1 | 6/2016 | McKernan |

FOREIGN PATENT DOCUMENTS

| EP | 0497272 A1 | 8/1992 |
| WO | 2016/189384 A1 | 12/2016 |
| WO | 2016/197258 A1 | 12/2016 |
| WO | 2019/118912 A1 | 6/2019 |

OTHER PUBLICATIONS

Gandelman et al. (International Journal of Mol. Sciences, vol. 12, pp. 9108-9124, 2011). (Year: 2011).*
McKernan et al. (bioRviv, Plant Biology, 28654/1-28654/23, Oct. 2015) (Year: 2015).*
Focke et al. (J. of Agricultural and Food Chemistry, vol. 61, pp. 2943-2949, 2013). (Year: 2013).*
Tighe et al. (J. Biomol Tech. vol. 32, No. 3, pp. 199-205, Sep. 2021) (Year: 2021).*
Jul. 15, 2021 Examination Report issued in European Patent Application No. 18839647.7.
Allen et al. (J. Forensic Investigation, vol. 4, No. 1, pp. 1-7, Feb. 19, 2016.) (Year: 2016).
Taura et al. (FEBS Letters, vol. 581, pp. 2929-2934, 2007). (Year: 2007).
Kitamura et al. (J. Nat. Med. vol. 71, pp. 86-95, Aug. 17, 2016). (Year: 2016).
Stiedl et al. (J. of Vet. Diagnostic Investigation, vol. 29, No. 2, pp. 176-180, 2017). (Year: 2017).
Barany, F., Genetic disease detection and DNA amplification using cloned thermostable ligase, Proc Natl Acad Sci USA, 88(1):189-93 (1991).
Barringer, K.J. et al., Blunt-end and single-strand ligations by *Escherichia coli* ligase: influence on an in vitro amplification scheme, Gene, 89(1):117-22 (1990).
De Meijer, E.P. et al., The inheritance of chemical phenotype in *Cannabis sativa* L, Genetics, 163(1):335-46 (2003).
Gandelman, O. et al., Loop-mediated amplification accelerated by stem primers, Int J Mol Sci, 12(12):9108-24 (2011).
Gill, P. and Ghaemi, A., Nucleic acid isothermal amplification technologies: a review, Nucleosides Nucleotides Nucleic Acids, 27(3):224-43 (2008).
Guatelli, J.C. et al., Isothermal, in vitro amplification of nucleic acids by a multienzyme reaction modeled after retroviral replication, Proc Natl Acad Sci USA, 87(5):1874-8 (1990).
Higuchi, R. et al., Kinetic PCR analysis: real-time monitoring of DNA amplification reactions, Biotechnology (NY), 11(9):1026-30 (1993).
Kato, Y. and Braunstein, G.D., Beta-core fragment is a major form of immunoreactive urinary chorionic gonadotropin in human pregnancy, J Clin Endocrinol Metab, 66(6):1197-201(1988).
Kitamura, M. et al., Development of Loop-Mediated Isothermal Amplification (LAMP) Assay for Rapid Detection of Cannabis sativa, Biol Pharm Bull. 39(7):1144-9 (2016).
Kitamura, M. et al., Rapid identification of drug-type strains in Cannabis sativa using loop-mediated isothermal amplification assay, J Nat Med, 71(1):86-95 (2017).
Kojoma, M. et al., DNA polymorphisms in the tetrahydrocannabinolic acid (THCA) synthase gene in "drug-type" and "fiber-type" *Cannabis sativa* L, Forensic Sci Int, 159(2-3):132-40 (2006).

(Continued)

*Primary Examiner* — Jeanine A Goldberg
(74) *Attorney, Agent, or Firm* — MH2 Technology Law Group, LLP

(57) ABSTRACT

The present disclosure provides methods and kits for characterizing *Cannabis* plants. Methods and kits of the present disclosure include detection/amplification of one or more enzymes involved in the production of cannabinoids, such as, for example, tetrahydrocannabinolic acid (THCA) synthase and/or cannabidiolic acid (CBDA) synthase.

20 Claims, 12 Drawing Sheets

Specification includes a Sequence Listing.

(56) References Cited

OTHER PUBLICATIONS

Kwoh, D.Y. et al., Transcription-based amplification system and detection of amplified human immunodeficiency virus type 1 with a bead-based sandwich hybridization format, Proc Natl Acad Sci USA, 86(4):1173-7 (1989).
Marks, M.D. et al., Identification of candidate genes affecting ?9-tetrahydrocannabinol biosynthesis in Cannabis sativa, J Exp Bot, 60(13):3715-26 (2009).
Nagamine, K. et al., Accelerated reaction by loop-mediated isothermal amplification using loop primers, Mol Cell Probes, 16(3):223-9 (2002).
Onofri, C. et al., Sequence heterogeneity of cannabidiolic-and tetrahydrocannabinolic acid-synthase in *Cannabis sativa* L. and its relationship with chemical phenotype, Phytochemistry, 116:57-68 (2015).
Staginnus, C, et al., A PCR marker linked to a THCA synthase polymorphism is a reliable tool to discriminate potentially THC-rich plants of *Cannabis sativa* L, J Forensic Sci, 59(4):919-26 (2014).
Walker, G.T. et al., Strand displacement amplification—an isothermal, in vitro DNA amplification technique, Nucleic Acids Res, 20(7):1691-6 (1992).
Walker, G.T., et al., Isothermal in vitro amplification of DNA by a restriction enzyme/DNA polymerase system, Proc Natl Acad Sci USA, 89(1):392-6 (1992).
Weiblen, G.D. et al., Gene duplication and divergence affecting drug content in Cannabis sativa, New Phytol, 208 (4):1241-50 (2015).
Wittwer, C.T. et al., Real-time multiplex PCR assays, Methods, 25(4):430-42 (2001).
Wu, D.Y. and Wallace, R.B., The ligation amplification reaction (LAR)-amplification of specific DNA sequences using sequential rounds of template-dependent ligation, Genomics, 4(4):560-9 (1989).
Cascini, F. et al., Analysis of THCA synthase gene expression in cannabis: a preliminary study by real-time quantitative PCR, Forensic Sci Int, 231(1-3):208-12 (2013).
International Search Report for PCT/US2018/065821 (Methods and Kits for Classifying Cannabinoid Production in Cannabis Plants, filed Dec. 14, 2018), issued by ISA/EP, 7 pages (Mar. 8, 2019).
Jeangkhwoa, P. et al., Identification of *Cannabis sativa* L. using the 1-kbTHCA synthase-fluorescence in situ hybridization probe, Sci Justice, 57(2):101-106 (2017).
Allen, L.N. et al., Complex Variability within the THCA and CBDA Synthase Genes in Cannabis Species, J Forensic Investigation, p. 1, retrieved from Internet: http://www.avensonline.org/wp-content/uploads/JFI-2330-0396-04--0029. pdf the wholedocument (2016).
Written Opinion for PCT/US2018/065821 (Methods and Kits for Classifying Cannabinoid Production in Cannabis Plants, filed Dec. 14, 2018), issued by ISA/EP, 8 pages (Mar. 8, 2019).
Aug. 23, 2023 Office Action issued in Canadian Patent Application No. 3,123,182.
Zhang, Y. et al. "Isothermal Amplification of Long, Discrete DNA Fragments Facilitated by Single-Stranded Binding Protein", Scientific Reports, 7(8497), pp. 1-9 (2017).
Jun. 30, 2022 Office Action issued in Canadian Patent Application No. 3,123,182.
Clinton Torres et al., "LAVA: An Open-Source Approach to Designing LAMP (Loop-Mediated Isothermal Amplification) DNA Signatures," BMC Bioinformatics, 2011 12:240, pp. 1-7.
Aug. 30, 2022 Office Action issued in European Patent Application No. 18 839 647.7.

\* cited by examiner

FIGURE 1
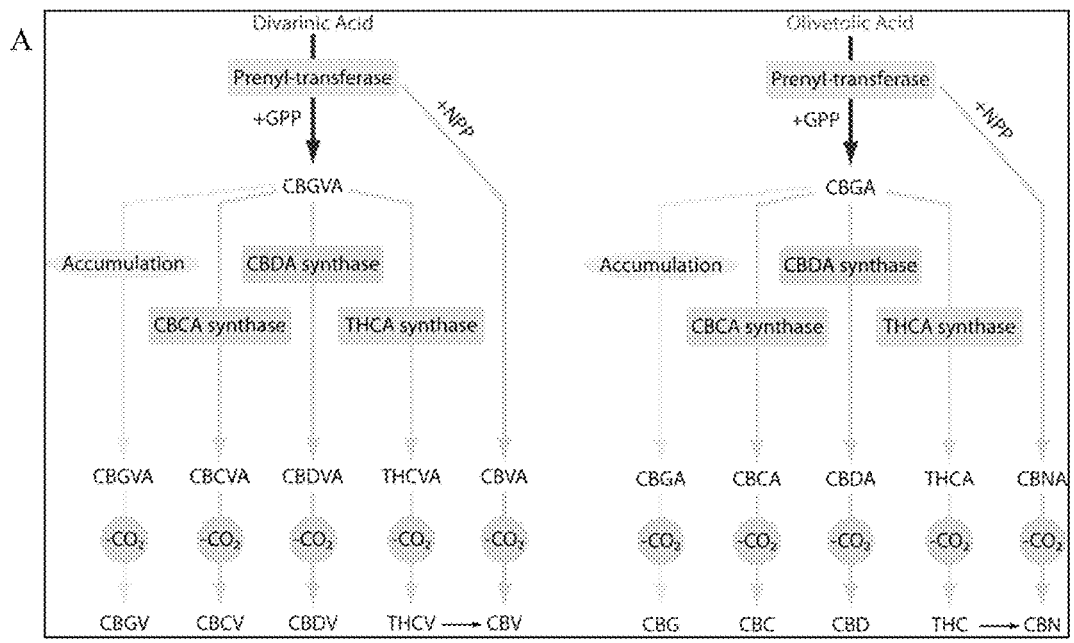
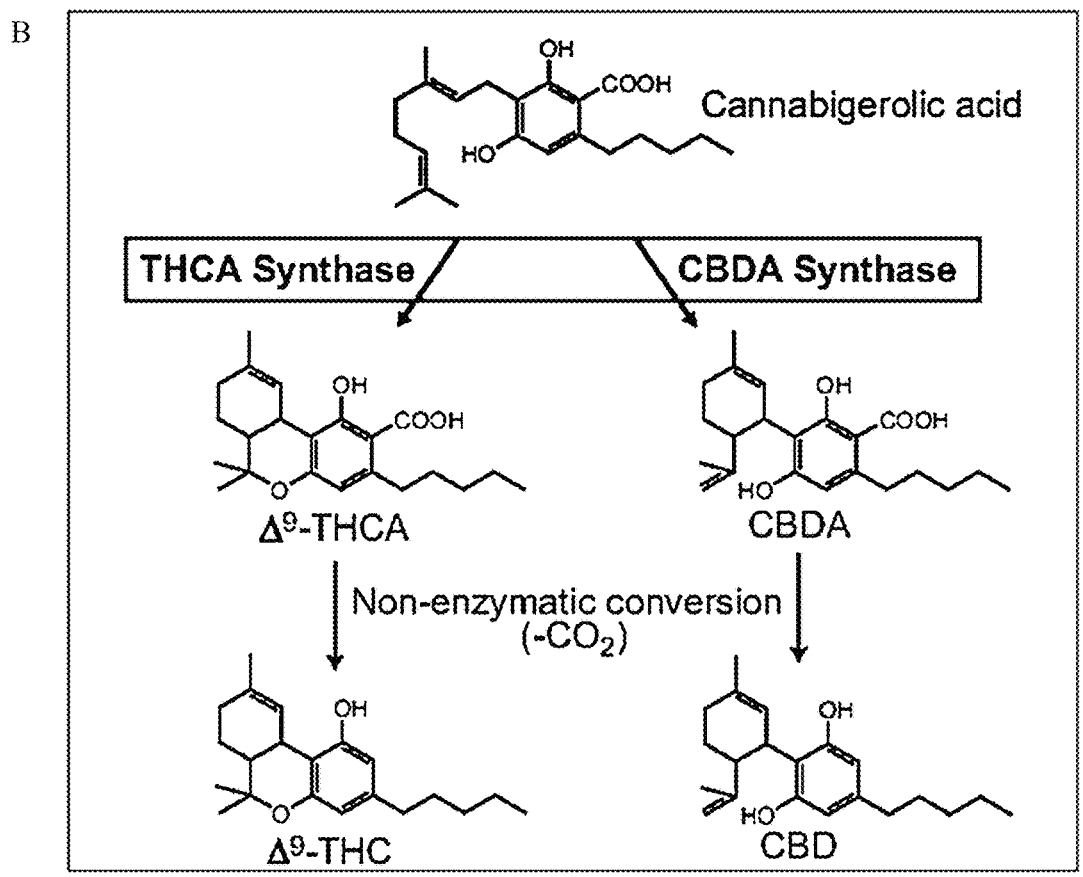

FIGURE 4

FIGURE 5
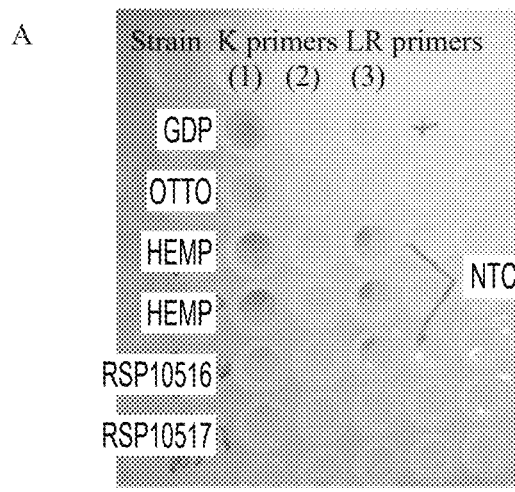
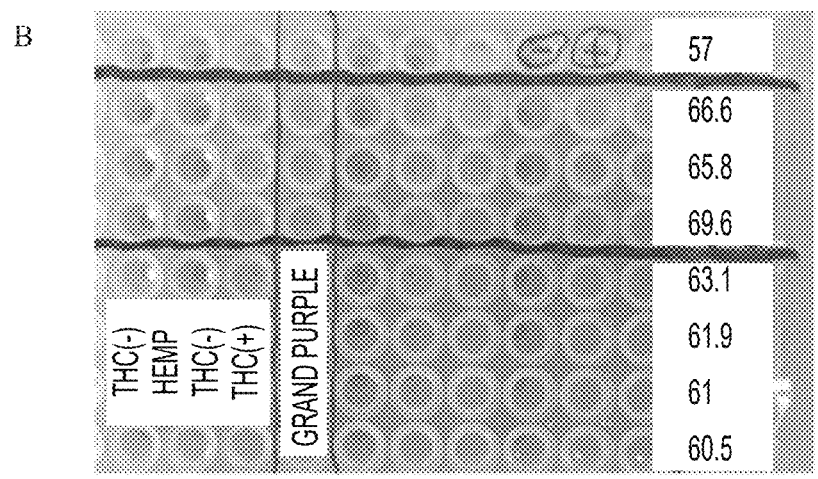

FIGURE 6

| Samples Mass Dispensaries | BarCode | THC | CBD | Well Location |
|---|---|---|---|---|
| White Fire OG_21NOV2016 | FR13698731 | 17.3 | 0.3 | A2 |
| MediHaze CBD_21NOV2016 | FR13697288 | 8.7 | 16.8 | B2 |
| Northern Lights #5 X Haze_21NOV2016 | FR13695854 | 23.2 | 0.3 | C2 |
| OG Kush CBD_21NOV2016 | FR13695841 | 4.5 | 9.8 | D2 |
| Phantom Cookies_21NOV2016 | FR13694935 | 19.4 | 0.1 | E2 |
| Critical Mass_21NOV2016 | FR13694452 | 9.84 | 13.41 | F2 |
| Super Silver Haze_21NOV2016 | FR13697319 | 27.4 | 0.3 | G2 |
| Canna-Tsu_21NOV2016 | FR13694429 | 6.5 | 13.5 | H2 |
| Grand Daddy Purple_21NOV2016 | FR13695383 | 17.5 | 0.2 | A3 |
| Herijuana_21NOV2016 | FR13698237 | 16.2 | 0.1 | B3 |
| California Dreaming_21NOV2016 | FR13697370 | 19.2 | 0.2 | C3 |
| Citrix_29NOV2016 | FR13695850 | 13.2 | 0.1 | D3 |
| Arcata Trainwreck_29NOV2016 | FR13698721 | 12.6 | 0.0 | E3 |
| Master Kush_29NOV2016 | FR13695413 | 16.3 | 0.1 | F3 |
| Harlox_29NOV2016 | FR13695415 | 13.8 | 0.1 | G3 |
| Hurricane_29NOV2016 | FR13697825 | 17.2 | 0.1 | H3 |
| Grape Stomper_29NOV2016 | FR13697344 | 15.4 | 0.1 | A4 |
| Erk Train X Deadhead OG_29NOV2016 | FR13697371 | 16.4 | 0.2 | B4 |
| Emerald Cup THC/CBD Samples | BarCode | THC | CBD | Well Location |
| MOTHERNLIGHTS CBD | FR09352163 | 6.72% | 9.69% | A5 |
| F-CANCER | FR09352247 | 6.10% | 13.39% | B6 |
| UNITY | FR09352367 | 10.02% | 11.13% | C6 |
| CANNATONIC | FR09352545 | 3.86% | 12.47% | D6 |
| GUERILLA MEDS | FR09352527 | 6.37% | 10.07% | E6 |
| TRIDENT | FR09352371 | 6.34% | 17.79% | F6 |
| SIERRA GOLD | FR09352486 | 8.18% | 12.60% | G6 |
| VITAMIN CBD | FR09352537 | 5.70% | 11.54% | H6 |
| HARLEQUIN CBD | FR09352134 | 3.53% | 9.14% | A7 |
| PINEAPPLETSU | FR09352298 | 6.67% | 16.70% | B7 |

| THC_BIP | CACACAAGCACGTATTGGGCTTAGTTTTCACCTTAAACTAACCT | SEQ ID NO: 8 | Desalt | 16uM |
|---|---|---|---|---|
| THC_FIP | GACTCGCATGATTAGTTTTCCTATCCTTATGTGTCCCAAAATCC | SEQ ID NO: 9 | Desalt | 16uM |
| THC_Loop1 | TCCCTATAATTGAGATACGCCAAT | SEQ ID NO: 10 | Desalt | 4uM |
| THC_F3 | ATGGGAACCATAATAAACTATAAAAGTCATT | SEQ ID NO: 11 | Desalt | 2uM |
| THC_B3 | TATGATTGTCTACACAGTTCTAATGTAGATTTTC | SEQ ID NO: 12 | Desalt | 2uM |

| CBD_BIP | CAATCTTAGATTCACCTCTGACACAAGACATGTGAAGGAGTGAC | SEQ ID NO: 13 | Desalt | 16uM |
|---|---|---|---|---|
| CBD_FIP | TGTATTGTCGAATTTAGGACAGACAATGCAACAAATCTAAAACTCGTA | SEQ ID NO: 14 | Desalt | 16uM |
| CBD_Loop1 | CAATGGGTTGTTTGAGTGT | SEQ ID NO: 15 | Desalt | 4uM |
| CBD_Loop2 | ACCCCAAAACCACTGT | SEQ ID NO: 16 | Desalt | 4uM |
| CBD_F3 | CTTCTCGCAATATATTCCCAAT | SEQ ID NO: 17 | Desalt | 2uM |
| CBD_B3 | GCATAGAATAGTGCCTTGGAT | SEQ ID NO: 18 | Desalt | 2uM |

| CBD_BIP | CAATCTTAGATTCACCTCTGACACAAGACATGTGAAGGAGTGAC | SEQ ID NO: 13 | Desalt | 16uM |
|---|---|---|---|---|
| CBD-NEG_FIP | TGTATTGTCGAATTTAGGACAGACAATGCAACAAATCTAAAACTTACA | SEQ ID NO: 19 | Desalt | 16uM |
| CBD_Loop1 | CAATGGGTTGTTTGAGTGT | SEQ ID NO: 15 | Desalt | 4uM |
| CBD_Loop2 | ACCCCAAAACCACTGT | SEQ ID NO: 16 | Desalt | 4uM |
| CBD_F3 | CTTCTCGCAATATATTCCCAAT | SEQ ID NO: 17 | Desalt | 2uM |
| CBD_B3 | GCATAGAATAGTGCCTTGGAT | SEQ ID NO: 18 | Desalt | 2uM |

| Accession code | 87 | 187 | 366 | 373 | 399 | 706 | 749 | 794 | 1179 | 1229 | 1395 | 1560 | Seq. ID | THC(V)A proportion |
|---|---|---|---|---|---|---|---|---|---|---|---|---|---|---|
| E33090 | T | A | A | G | A | G | C | A | A | G | T | G | 1/1 | unknown |
| 55.22.7.2.2 | T | A | A | G | A | G | C | A | A | G | T | G | 1/1 | 93.1% |
|  | C | A | A | G | A | G | C | A | A | G | T | G | 1/2 |  |
| 55.24.4.34.7 | T | A | A | G | A | G | C | A | A | G | T | G | 1/1 | 89.1% |
| 2009.27.44.2.19 | T | A | A | G | A | C | C | A | A | G | T | G | 1/3 | 11.1% |
| 55.28.1.4.12 | T | A | A | G | A | G | C | A | A | G | T | G | 1/1 | 55.0% |
| 2010.24a.35/T | T | C | T | G | G | G | C | A | T | G | T | G | 3 | 96.2% |
| M110 | T | A | A | G | A | G | C | A | A | G | T | G | 1/1 | 96.4% |
|  | T | A | T | C | A | G | C | A | A | A | A | A | 2/1 |  |
|  | T | A | T | C | A | G | C | A | A | A | T | G | 2/2 |  |
|  | T | A | T | C | A | G | C | A | A | A | T | G | 2/3 |  |
|  | T | A | A | G | A | G | C | G | A | A | A | A | 4 |  |
| M124 | T | C | T | G | G | G | C | A | T | G | T | G | 3 | 98.6% |
|  | T | A | A | G | A | G | A | A | A | G | T | G | 1/4 |  |
| M128 | T | A | A | G | A | G | C | A | A | G | T | G | 1/1 | 96.5% |
|  | T | C | T | G | G | G | C | A | T | G | T | G | 3 |  |
|  |  | 63 Leu ↓ Leu |  | 125 Val ↓ Leu |  | 236 Glu ↓ Gln | 250 Ala ↓ Asp | 265 Glu ↓ Gly |  | 410 Gly ↓ Glu |  |  |  |  |

Onofri et al., (2015) *Phytochemistry*, 116:57-68, PMID: 25865737

SEQUENCE LISTING

```
<160> NUMBER OF SEQ ID NOS: 27

<210> SEQ ID NO 1
<211> LENGTH: 2121
<212> TYPE: DNA
<213> ORGANISM: Cannabis sativa

<400> SEQUENCE: 1
atgggaacca taataaacta taaaagtcat tatgtgtact tgctaccata ggcacctata     60
tcccacaaac tagctaccat agccaatttc ttttttgttt ccaatatcca attttttattg    120 atgccaaact attcaatgta caatgtacat ttattttcaa taagggcttc acctaacaaa    180
```

```
ggtgcctaat tttagttgat ttatttttta tcacatgtga ctatttaatg actatcaaat      240
tataaaatat ttaagtcaat ttatttgccc caactccaat atataatatt ataaatagga      300
tagttctcaa ttcctaataa ttcaaaaaat cattaggact gaagaaaaat gaattgctca      360
gcattttcct tttggtttgt ttgcaaaata atattttttct ttctctcatt ccatatccaa     420
atttcaatag ctaatcctcg agaaaacttc cttaaatgct tctcaaaaca tattcccaac      480
aatgtagcaa atccaaaact cgtatacact caacacgacc aattgtatat gtctatcctg      540
aattcgacaa tacaaaatct tagattcatc tctgatacaa ccccaaaacc actcgttatt      600
gtcactcctt caaataactc ccatatccaa gcaactattt tatgctctaa gaaagttggc      660
ttgcagattc gaactcgaag cggtggccat gatgctgagg gtatgtccta catatctcaa      720
gtcccatttg ttgtagtaga cttgagaaac atgcattcga tcaaaataga tgttcatagc      780
caaactgcgt gggttgaagc cggagctacc cttggagaag tttattattg gatcaatgag      840
aagaatgaga atcttagttt tcctggtggg tattgcccta ctgttggcgt aggtggacac      900
tttagtggag gaggctatgg agcattgatg cgaaattatg gccttgcggc tgataatatt      960
attgatgcac acttagtcaa tgttgatgga aaagttctag atcgaaaatc catgggagaa     1020
gatctgtttt gggctatacg tggtggtgga ggagaaaact ttggaatcat gcagcatgg      1080 aaaatcaaac tggttgatgt cccatcaaag tctactatat tcagtgttaa aaagaacatg     1140
gagatacatg gcttgtcaa gttatttaac aaatggcaaa atattgctta caagtatgac     1200
aaagatttag tactcatgac tcacttcata acaaagaata ttacagataa tcatgggaag     1260
aataagacta cagtacatgg ttacttctct tcaattttc atggtggagt ggatagtcta     1320
gtcgacttga tgaacaagag ctttcctgag ttgggtatta aaaaaactga ttgcaaagaa     1380
tttagctgga ttgatacaac catcttctac agtggtgttg taaattttaa cactgctaat     1440
tttaaaaagg aaattttgct tgatagatca gctgggaaga gacggctttt ctcaattaag     1500
ttagactatg ttaagaaacc aattccagaa actgcaatgg tcaaaatttt ggaaaaatta     1560
tatgaagaag atgtaggagc tggggtgttg tacccttacg gtggtataat ggaggagatt     1620
tcagaatcag caattccatt ccctcatcga gctggaataa tgtatgaact tggtacact      1680 gcttcctggg agaagcaaga agataatgaa aagcatataa actgggttcg aagtgtttat     1740
aattttacga ctccttatgt gtcccaaaat ccaagattgg cgtatctcaa ttataggac      1800 cttgatttag gaaaaactaa tcatgcgagt cctaataatt acacacaagc acgtatttgg     1860
ggtgaaaagt attttggtaa aaattttaac aggttagtta aggtgaaaac taaagttgat     1920
cccaataatt tttttagaaa cgaacaaagt atcccacctc ttccaccgca tcatcattaa     1980
ttatctttaa atagatatat ttcccttatc aattagttaa tcattatacc atacatacat     2040
ttattgtata tagtttatct actcatatta tgtatgctcc caagtatgaa aatctacatt     2100
agaactgtgt agacaatcat a                                                2121
```

<210> SEQ ID NO 2
<211> LENGTH: 1941
<212> TYPE: DNA
<213> ORGANISM: Cannabis sativa

<400> SEQUENCE: 2

```
gatatatatc tcacacggat gcacctaaca atgatgccta attttgtga atttttttta       60 ccacatgact taatgatatc aaattatgaa atatttagtt aatttatttg cccctgctcc      120
aatatataaa gctataaata ggatagttct taatccatag taattcaaaa ttcattagaa      180
```

-continued

| | |
|---|---|
| ctaaagaaaa atgaagtgct caacattctc cttttggttt gtttgcaaga taatattttt | 240 |
| cttttctca ttcaatatcc aaacttccat tgctaatcct cgagaaaact tccttaaatg | 300 |
| cttctcgcaa tatattccca ataatgcaac aaatctaaaa ctcgtataca ctcaaaacaa | 360 |
| cccattgtat atgtctgtcc taaattcgac aatacacaat cttagattca cctctgacac | 420 |
| aaccccaaaa ccacttgtta tcgtcactcc ttcacatgtc tctcatatcc aaggcactat | 480 |
| tctatgctcc aagaaagttg gcttgcagat tcgaactcga agtggtggtc atgattctga | 540 |
| gggcatgtcc tacatatctc aagtcccatt tgttatagta gacttgagaa acatgcgttc | 600 |
| aatcaaaata gatgttcata gccaaactgc atgggttgaa gccggagcta cccttggaga | 660 |
| agtttattat tgggttaatg agaaaaatga gaatcttagt ttggcggctg gtattgccc | 720 |
| tactgtttgc gcaggtggac actttggtgg aggaggctat ggaccattga tgagaaacta | 780 |
| tggcctcgcg gctgataata tcattgatgc acacttagtc aacgttcatg gaaaagtgct | 840 |
| agatcgaaaa tctatggggg aagatctctt tgggcttta cgtggtggtg gagcagaaag | 900 |
| cttcggaatc attgtagcat ggaaaattag actggttgct gtcccaaagt ctactatgtt | 960 |
| tagtgttaaa aagatcatgg agatacatga gcttgtcaag ttagttaaca atggcaaaa | 1020 |
| tattgcttac aagtatgaca agatttatt actcatgact cacttcataa ctaggaacat | 1080 |
| tacagataat caaggaaga ataagacagc aatacacact tacttctctt cagttttcct | 1140 |
| tggtggagtg gatagtctag tcgacttgat gaacaagagt tttcctgagt tgggtattaa | 1200 |
| aaaaacggat tgcagacaat tgagctggat tgatactatc atcttctata gtggtgttgt | 1260 |
| aaattacgac actgataatt ttaacaagga aattttgctt gatagatccg ctgggcagaa | 1320 |
| cggtgctttc aagattaagt tagactacgt taagaaacca attccagaat ctgtatttgt | 1380 |
| ccaaattttg gaaaaattat atgaagaaga tataggagct gggatgtatg cgttgtaccc | 1440 |
| ttacggtggt ataatggatg agatttcaga atcagcaatt ccattccctc atcgagctgg | 1500 |
| aatcttgtat gagttatggt acatatgtag ttgggagaag caagaagata acgaaaagca | 1560 |
| tctaaactgg attagaaata tttataactt catgactcct tatgtgtcca aaaatccaag | 1620 |
| attggcatat ctcaattata gagaccttga tataggaata aatgatccca agaatccaaa | 1680 |
| taattacaca caagcacgta tttggggtga gaagtatttt ggtaaaaatt ttgacaggct | 1740 |
| agtaaaagtg aaaccctgg ttgatcccaa taacttttt agaaacgaac aaagcatccc | 1800 |
| acctcttcca cggcatcgtc attaatgatc ttaaatagat cttttctct tattaattag | 1860 |
| tccttataat atacatatat tgattatata tataaaaata gtttgtccgg gtgtactgtg | 1920 |
| tatgcgatat atatctcaca c | 1941 |

<210> SEQ ID NO 3
<211> LENGTH: 4
<212> TYPE: DNA
<213> ORGANISM: Cannabis sativa

<400> SEQUENCE: 3

| | |
|---|---|
| cgta | 4 |

<210> SEQ ID NO 4
<211> LENGTH: 1158
<212> TYPE: DNA
<213> ORGANISM: Cannabis sativa

<400> SEQUENCE: 4

-continued

```
atgaatcatc ttcgtgctga gggtccggcc tccgttctcg ccattggcac cgccaatccg      60
gagaacattt tattacaaga tgagtttcct gactactatt ttcgcgtcac caaaagtgaa     120
cacatgactc aactcaaaga aaagtttcga aaaatatgtg acaaaagtat gataaggaaa     180
cgtaactgtt tcttaaatga agaacaccta aagcaaaacc caagattggt ggagcacgag     240
atgcaaactc tggatgcacg tcaagacatg ttggtagttg aggttccaaa acttgggaag     300
gatgcttgtg caaaggccat caagaatgg ggtcaaccca agtctaaaat cactcattta      360
atcttcacta gcgcatcaac cactgacatg cccggtgcag actaccattg cgctaagctt     420
ctcggactga gtccctcagt gaagcgtgtg atgatgtatc aactaggctg ttatggtggt     480
ggaaccgttc tacgcattgc caaggacata gcagagaata caaaggcgc acgagttctc      540 gccgtgtgtt gtgacataat ggcttgcttg tttcgtgggc cttcagagtc tgacctcgaa     600
ttactagtgg acaagctat ctttggtgat ggggctgctg cggtgattgt tggagctgaa      660
cccgatgagt cagttgggga aaggccgata tttgagttgg tgtcaactgg gcaaacaatc     720
ttaccaaact cggaaggaac tattgggga catataaggg aagcaggact gatatttgat      780
ttacataagg atgtgcctat gttgatctct aataatattg agaatgttt gattgaggca      840 tttactccta ttgggattag tgattggaac tccatatttt ggattacaca cccaggtggg     900
aaagctattt tggacaaagt ggaggagaag ttgcatctaa agagtgataa gtttgtggat     960
tcacgtcatg tgctgagtga gcatgggaat atgtctagct caactgtctt gtttgttatg    1020
gatgagttga ggaagaggtc gttggaggaa gggaagtcta ccactggaga tggatttgag    1080
tggggtgttc tttttgggtt tggaccaggt ttgactgtcg aaagagtggt cgtgcgtagt    1140
gttcccatca aatattaa                                                  1158
```

<210> SEQ ID NO 5
<211> LENGTH: 1869
<212> TYPE: DNA
<213> ORGANISM: Cannabis sativa

<400> SEQUENCE: 5

```
atgcagtgca tagctttca ccaatttgct tcatcatcat ccctccctat ttggagtagt       60
attgataatc gttttacacc aaaaacttct attacttcta tttcaaaacc aaaaccaaaa     120
ctaaaatcaa aatcaaactt gaaatcgaga tcgagatcaa gtacttgcta ctccatacaa     180
tgtactgtgg tcgataaccc tagttctacg attactaata atagtgatcg aagatcagcc     240
aactatggac ctcccatttg gtcttttgat tttgttcaat ctcttccaat ccaatataag     300
ggtgaatctt atacaagtcg attaaataag ttggagaaag atgtgaaaag gatgctaatt     360
ggagtggaaa actctttagc ccaacttgaa ctaattgata caatacaaag acttggaata    420
tcttatcgtt ttgaaaatga aatcatttct attttgaaag aaaaattcac caataataat     480
gacaacccta atcctaatta tgatttatat gctactgctc tccaatttag gcttctacgc    540
caatatggat ttgaagtacc tcaagaaatt ttcaataatt ttaaaaatca agacagga       600 gagttcaagg caaatataag taatgatatt atgggagcat gggcttata tgaagcttca     660 ttccatggga aaaagggtga agtattttg gaagaagcaa gattttcac aacaaaatgt      720 ctcaaaaaat acaaattaat gtcaagtagt aataataata atatgacatt aatatcatta    780
ttagtgaatc atgctttgga gatgccactt caatggagaa tcacaagatc agaagctaaa    840
tggtttattg agaaaatata tgaaagaaaa caagacatga atccaacttt acttgagttt    900
gccaaattgg atttcaatat gctgcaatca acatatcaag aggagctcaa agtactctct    960
```

```
aggtggtgga aggattctaa acttggagag aaattgcctt tcgttagaga tagattggtg    1020
gagtgtttct tatggcaagt tggagtaaga tttgagccac aattcagtta ctttagaata    1080
atggatacaa aactctatgt tctattaaca ataattgatg atatgcatga catttatgga    1140
acattggagg aactacaact tttcactaat gctcttcaaa gatgggattt gaaagaatta    1200 gataaaattac cagattatat gaagacagct ttctacttta catacaattt cacaaatgaa    1260
ttggcatttg atgtattaca agaacatggt tttgttcaca ttgaatactt caagaaactg    1320
atggtagagt tgtgtaaaca tcatttgcaa gaggcaaaat ggttttatag tggatacaaa    1380
ccaacattgc aagaatatgt tgagaatgga tggttgtctg tgggaggaca agttattctt    1440
atgcatgcat atttcgcttt tacaaatcct gttaccaaag aggcattgga atgtctaaaa    1500
gacggtcatc ctaacatagt tcgccatgca tcgataatat tacgacttgc agatgatcta    1560
ggaacattgt cggatgaact gaaaagaggc gatgttccta aatcaattca atgttatatg    1620
cacgatactg gtgcttctga agatgaagct cgtgagcaca taaaatattt aataagtgaa    1680
tcatggaagg agatgaataa tgaagatgga aatattaact cttttttctc aaatgaattt    1740
gttcaagttt gccaaaatct tggtagagcg tcacaattca tataccagta tggcgatgga    1800
catgcttctc agaataatct atcgaaagag cgcgttttag ggttgattat tactcctatc    1860
cccatgtaa                                                              1869

<210> SEQ ID NO 6
<211> LENGTH: 351
<212> TYPE: DNA
<213> ORGANISM: Cannabis sativa

<400> SEQUENCE: 6
catagcgact atcgtgatgg gaaccataat aaactataaa agtcattatg tgtacttgct      60
accataggca cctatatccc acaaactagc taccatagcc aatttctttt ttgtttccaa     120
tatccaattt ttattgatgc caaactattc aatgtacaat gtacatttat tttcaataag     180
ggcttcacct aacaaaggtg cctaattttta gttgatttat tttttatcac atgtgactat     240
ttaatgacta tcaaattata aaatatttaa gtcaattat ttgccccaac tccaatatat      300
aatattataa ataggatagt tctcaattcc taataattca aaaaatcatt a              351

<210> SEQ ID NO 7
<211> LENGTH: 132
<212> TYPE: DNA
<213> ORGANISM: Cannabis sativa

<400> SEQUENCE: 7
ttatcaatta gttaatcatt ataccataca tacatttatt gtatatagtt tatctactca      60
tattatgtat gctcccaagt atgaaaatct acattagaac tgtgtagaca atcatacata     120
gcgactatcg tg                                                          132

<210> SEQ ID NO 8
<211> LENGTH: 45
<212> TYPE: DNA
<213> ORGANISM: Artificial Sequence
<220> FEATURE:
<223> OTHER INFORMATION: Synthetic primer

<400> SEQUENCE: 8
cacacaagca cgtatttggg ctttagtttt caccttaact aacct                      45
```

<210> SEQ ID NO 9
<211> LENGTH: 45
<212> TYPE: DNA
<213> ORGANISM: Artificial Sequence
<220> FEATURE:
<223> OTHER INFORMATION: Synthetic primer

<400> SEQUENCE: 9
gactcgcatg attagttttt cctatcctta tgtgtcccaa aatcc    45

<210> SEQ ID NO 10
<211> LENGTH: 24
<212> TYPE: DNA
<213> ORGANISM: Artificial Sequence
<220> FEATURE:
<223> OTHER INFORMATION: Synthetic primer

<400> SEQUENCE: 10
tccctataat tgagatacgc caat    24

<210> SEQ ID NO 11
<211> LENGTH: 31
<212> TYPE: DNA
<213> ORGANISM: Artificial Sequence
<220> FEATURE:
<223> OTHER INFORMATION: Synthetic primer

<400> SEQUENCE: 11
atgggaacca taataaacta taaaagtcat t    31

<210> SEQ ID NO 12
<211> LENGTH: 34
<212> TYPE: DNA
<213> ORGANISM: Artificial Sequence
<220> FEATURE:
<223> OTHER INFORMATION: Synthetic primer

<400> SEQUENCE: 12
tatgattgtc tacacagttc taatgtagat tttc    34

<210> SEQ ID NO 13
<211> LENGTH: 44
<212> TYPE: DNA
<213> ORGANISM: Artificial Sequence
<220> FEATURE:
<223> OTHER INFORMATION: Synthetic primer

<400> SEQUENCE: 13
caatcttaga ttcacctctg acacaagaca tgtgaaggag tgac    44

<210> SEQ ID NO 14
<211> LENGTH: 48
<212> TYPE: DNA
<213> ORGANISM: Artificial Sequence
<220> FEATURE:
<223> OTHER INFORMATION: Synthetic primer

<400> SEQUENCE: 14
tgtattgtcg aatttaggac agacaatgca acaaatctaa aactcgta    48

<210> SEQ ID NO 15
<211> LENGTH: 20
<212> TYPE: DNA
<213> ORGANISM: Artificial Sequence
<220> FEATURE:
<223> OTHER INFORMATION: Synthetic primer -continued

```
<400> SEQUENCE: 15
caatgggttg ttttgagtgt                                                    20

<210> SEQ ID NO 16
<211> LENGTH: 17
<212> TYPE: DNA
<213> ORGANISM: Artificial Sequence
<220> FEATURE:
<223> OTHER INFORMATION: Synthetic primer

<400> SEQUENCE: 16
accccaaaac cacttgt                                                       17

<210> SEQ ID NO 17
<211> LENGTH: 22
<212> TYPE: DNA
<213> ORGANISM: Artificial Sequence
<220> FEATURE:
<223> OTHER INFORMATION: Synthetic primer

<400> SEQUENCE: 17
cttctcgcaa tatattccca at                                                 22

<210> SEQ ID NO 18
<211> LENGTH: 21
<212> TYPE: DNA
<213> ORGANISM: Artificial Sequence
<220> FEATURE:
<223> OTHER INFORMATION: Synthetic primer

<400> SEQUENCE: 18
gcatagaata gtgccttgga t                                                  21

<210> SEQ ID NO 19
<211> LENGTH: 48
<212> TYPE: DNA
<213> ORGANISM: Artificial Sequence
<220> FEATURE:
<223> OTHER INFORMATION: Synthetic primer

<400> SEQUENCE: 19
tgtattgtcg aatttaggac agacaatgca acaaatctaa aacttaca                     48

<210> SEQ ID NO 20
<211> LENGTH: 2153
<212> TYPE: DNA
<213> ORGANISM: Cannabis sp.
<220> FEATURE:
<221> NAME/KEY: CDS
<222> LOCATION: (365)..(1993)

<400> SEQUENCE: 20
catagcgact atcgtgatgg gaaccataat aaactataaa agtcattatg tgtacttgct         60
accataggca cctatatccc acaaactagc taccatagcc aatttctttt ttgtttccaa        120
tatccaattt ttattgatgc caaactattc aatgtacaat gtacatttat tttcaataag        180
ggcttcacct aacaaaggtg cctaatttta gttgatttat ttttatcac atgtgactat         240 ttaatgacta tcaaattata aatatttaa gtcatttat ttgccccaac tccaatatat         300
aatattataa ataggatagt tctcaattcc taataattca aaaaatcatt aggactgaag        360 aaaa atg aat tgc tca gca ttt tcc ttt tgg ttt gtt tgc aaa ata ata        409
     Met Asn Cys Ser Ala Phe Ser Phe Trp Phe Val Cys Lys Ile Ile
     1               5                   10                  15
```

```
ttt ttc ttt ctc tca ttc cat atc caa att tca ata gct aat cct cga    457
Phe Phe Phe Leu Ser Phe His Ile Gln Ile Ser Ile Ala Asn Pro Arg
            20                  25                  30 gaa aac ttc ctt aaa tgc ttc tca aaa cat att ccc aac aat gta gca    505
Glu Asn Phe Leu Lys Cys Phe Ser Lys His Ile Pro Asn Asn Val Ala
        35                  40                  45 aat cca aaa ctc gta tac act caa cac gac caa ttg tat atg tct atc    553
Asn Pro Lys Leu Val Tyr Thr Gln His Asp Gln Leu Tyr Met Ser Ile
    50                  55                  60 ctg aat tcg aca ata caa aat ctt aga ttc atc tct gat aca acc cca    601
Leu Asn Ser Thr Ile Gln Asn Leu Arg Phe Ile Ser Asp Thr Thr Pro
65                  70                  75 aaa cca ctc gtt att gtc act cct tca aat aac tcc cat atc caa gca    649
Lys Pro Leu Val Ile Val Thr Pro Ser Asn Asn Ser His Ile Gln Ala
80                  85                  90                  95 act att tta tgc tct aag aaa gtt ggc ttg cag att cga act cga agc    697
Thr Ile Leu Cys Ser Lys Lys Val Gly Leu Gln Ile Arg Thr Arg Ser
                100                 105                 110 ggt ggc cat gat gct gag ggt atg tcc tac ata tct caa gtc cca ttt    745
Gly Gly His Asp Ala Glu Gly Met Ser Tyr Ile Ser Gln Val Pro Phe
            115                 120                 125 gtt gta gta gac ttg aga aac atg cat tcg atc aaa ata gat gtt cat    793
Val Val Val Asp Leu Arg Asn Met His Ser Ile Lys Ile Asp Val His
        130                 135                 140 agc caa act gcg tgg gtt gaa gcc gga gct acc ctt gga gaa gtt tat    841
Ser Gln Thr Ala Trp Val Glu Ala Gly Ala Thr Leu Gly Glu Val Tyr
    145                 150                 155 tat tgg atc aat gag aag aat gag aat ctt agt ttt cct ggt ggg tat    889
Tyr Trp Ile Asn Glu Lys Asn Glu Asn Leu Ser Phe Pro Gly Gly Tyr
160                 165                 170                 175 tgc cct act gtt ggc gta ggt gga cac ttt agt gga gga ggc tat gga    937
Cys Pro Thr Val Gly Val Gly Gly His Phe Ser Gly Gly Gly Tyr Gly
                180                 185                 190 gca ttg atg cga aat tat ggc ctt gcg gct gat aat att att gat gca    985
Ala Leu Met Arg Asn Tyr Gly Leu Ala Ala Asp Asn Ile Ile Asp Ala
            195                 200                 205 cac tta gtc aat gtt gat gga aaa gtt cta gat cga aaa tcc atg gga   1033
His Leu Val Asn Val Asp Gly Lys Val Leu Asp Arg Lys Ser Met Gly
        210                 215                 220 gaa gat ctg ttt tgg gct ata cgt ggt ggt gga gaa aac ttt gga       1081
Glu Asp Leu Phe Trp Ala Ile Arg Gly Gly Gly Glu Asn Phe Gly
    225                 230                 235 atc att gca gca tgg aaa atc aaa ctg gtt gat gtc cca tca aag tct   1129
Ile Ile Ala Ala Trp Lys Ile Lys Leu Val Asp Val Pro Ser Lys Ser
240                 245                 250                 255 act ata ttc agt gtt aaa aag aac atg gag ata cat ggg ctt gtc aag   1177
Thr Ile Phe Ser Val Lys Lys Asn Met Glu Ile His Gly Leu Val Lys
                260                 265                 270 tta ttt aac aaa tgg caa aat att gct tac aag tat gac aaa gat tta   1225
Leu Phe Asn Lys Trp Gln Asn Ile Ala Tyr Lys Tyr Asp Lys Asp Leu
            275                 280                 285 gta ctc atg act cac ttc ata aca aag aat att aca gat aat cat ggg   1273
Val Leu Met Thr His Phe Ile Thr Lys Asn Ile Thr Asp Asn His Gly
        290                 295                 300 aag aat aag act aca gta cat ggt tac ttc tct tca att ttt cat ggt   1321
Lys Asn Lys Thr Thr Val His Gly Tyr Phe Ser Ser Ile Phe His Gly
    305                 310                 315 gga gtg gat agt cta gtc gac ttg atg aac aag agc ttt cct gag ttg   1369
Gly Val Asp Ser Leu Val Asp Leu Met Asn Lys Ser Phe Pro Glu Leu
```

```
                320                 325                 330                 335
ggt att aaa aaa act gat tgc aaa gaa ttt agc tgg att gat aca acc    1417
Gly Ile Lys Lys Thr Asp Cys Lys Glu Phe Ser Trp Ile Asp Thr Thr
                340                 345                 350 atc ttc tac agt ggt gtt gta aat ttt aac act gct aat ttt aaa aag    1465
Ile Phe Tyr Ser Gly Val Val Asn Phe Asn Thr Ala Asn Phe Lys Lys
                355                 360                 365 gaa att ttg ctt gat aga tca gct ggg aag aag acg gct ttc tca att    1513
Glu Ile Leu Leu Asp Arg Ser Ala Gly Lys Lys Thr Ala Phe Ser Ile
                370                 375                 380 aag tta gac tat gtt aag aaa cca att cca gaa act gca atg gtc aaa    1561
Lys Leu Asp Tyr Val Lys Lys Pro Ile Pro Glu Thr Ala Met Val Lys
                385                 390                 395 att ttg gaa aaa tta tat gaa gaa gat gta gga gct ggg gtg ttg tac    1609
Ile Leu Glu Lys Leu Tyr Glu Glu Asp Val Gly Ala Gly Val Leu Tyr
400                 405                 410                 415 cct tac ggt ggt ata atg gag gag att tca gaa tca gca att cca ttc    1657
Pro Tyr Gly Gly Ile Met Glu Glu Ile Ser Glu Ser Ala Ile Pro Phe
                420                 425                 430 cct cat cga gct gga ata atg tat gaa ctt tgg tac act gct tcc tgg    1705
Pro His Arg Ala Gly Ile Met Tyr Glu Leu Trp Tyr Thr Ala Ser Trp
                435                 440                 445 gag aag caa gaa gat aat gaa aag cat ata aac tgg gtt cga agt gtt    1753
Glu Lys Gln Glu Asp Asn Glu Lys His Ile Asn Trp Val Arg Ser Val
                450                 455                 460 tat aat ttt acg act cct tat gtg tcc caa aat cca aga ttg gcg tat    1801
Tyr Asn Phe Thr Thr Pro Tyr Val Ser Gln Asn Pro Arg Leu Ala Tyr
                465                 470                 475 ctc aat tat agg gac ctt gat tta gga aaa act aat cat gcg agt cct    1849
Leu Asn Tyr Arg Asp Leu Asp Leu Gly Lys Thr Asn His Ala Ser Pro
480                 485                 490                 495 aat aat tac aca caa gca cgt att tgg ggt gaa aag tat ttt ggt aaa    1897
Asn Asn Tyr Thr Gln Ala Arg Ile Trp Gly Glu Lys Tyr Phe Gly Lys
                500                 505                 510 aat ttt aac agg tta gtt aag gtg aaa act aaa gtt gat ccc aat aat    1945
Asn Phe Asn Arg Leu Val Lys Val Lys Thr Lys Val Asp Pro Asn Asn
                515                 520                 525 ttt ttt aga aac gaa caa agt atc cca cct ctt cca ccg cat cat cat    1993
Phe Phe Arg Asn Glu Gln Ser Ile Pro Pro Leu Pro Pro His His His
                530                 535                 540 taattatctt taaatagata tatttccctt atcaattagt taatcattat accatacata    2053
catttattgt atatagttta tctactcata ttatgtatgc tcccaagtat gaaaatctac    2113
attagaactg tgtagacaat catacatagc gactatcgtg                           2153

<210> SEQ ID NO 21
<211> LENGTH: 543
<212> TYPE: PRT
<213> ORGANISM: Cannabis sp.

<400> SEQUENCE: 21

Met Asn Cys Ser Ala Phe Ser Phe Trp Phe Val Cys Lys Ile Ile Phe
1               5                   10                  15

Phe Phe Leu Ser Phe His Ile Gln Ile Ser Ile Ala Asn Pro Arg Glu
                20                  25                  30

Asn Phe Leu Lys Cys Phe Ser Lys His Ile Pro Asn Asn Val Ala Asn
            35                  40                  45

Pro Lys Leu Val Tyr Thr Gln His Asp Gln Leu Tyr Met Ser Ile Leu
        50                  55                  60
```

```
Asn Ser Thr Ile Gln Asn Leu Arg Phe Ile Ser Asp Thr Thr Pro Lys
 65                  70                  75                  80

Pro Leu Val Ile Val Thr Pro Ser Asn Ser His Ile Gln Ala Thr
                     85                  90                  95

Ile Leu Cys Ser Lys Lys Val Gly Leu Gln Ile Arg Thr Arg Ser Gly
                100                 105                 110

Gly His Asp Ala Glu Gly Met Ser Tyr Ile Ser Gln Val Pro Phe Val
            115                 120                 125

Val Val Asp Leu Arg Asn Met His Ser Ile Lys Ile Asp Val His Ser
    130                 135                 140

Gln Thr Ala Trp Val Glu Ala Gly Ala Thr Leu Gly Glu Val Tyr Tyr
145                 150                 155                 160

Trp Ile Asn Glu Lys Asn Glu Asn Leu Ser Phe Pro Gly Gly Tyr Cys
                165                 170                 175

Pro Thr Val Gly Val Gly Gly His Phe Ser Gly Gly Tyr Gly Ala
                180                 185                 190

Leu Met Arg Asn Tyr Gly Leu Ala Ala Asp Asn Ile Ile Asp Ala His
        195                 200                 205

Leu Val Asn Val Asp Gly Lys Val Leu Asp Arg Lys Ser Met Gly Glu
210                 215                 220

Asp Leu Phe Trp Ala Ile Arg Gly Gly Gly Gly Glu Asn Phe Gly Ile
225                 230                 235                 240

Ile Ala Ala Trp Lys Ile Lys Leu Val Asp Val Pro Ser Lys Ser Thr
                245                 250                 255

Ile Phe Ser Val Lys Lys Asn Met Glu Ile His Gly Leu Val Lys Leu
                260                 265                 270

Phe Asn Lys Trp Gln Asn Ile Ala Tyr Lys Tyr Asp Lys Asp Leu Val
        275                 280                 285

Leu Met Thr His Phe Ile Thr Lys Asn Ile Thr Asp Asn His Gly Lys
    290                 295                 300

Asn Lys Thr Thr Val His Gly Tyr Phe Ser Ser Ile Phe His Gly Gly
305                 310                 315                 320

Val Asp Ser Leu Val Asp Leu Met Asn Lys Ser Phe Pro Glu Leu Gly
                325                 330                 335

Ile Lys Lys Thr Asp Cys Lys Glu Phe Ser Trp Ile Asp Thr Thr Ile
                340                 345                 350

Phe Tyr Ser Gly Val Val Asn Phe Asn Thr Ala Asn Phe Lys Lys Glu
        355                 360                 365

Ile Leu Leu Asp Arg Ser Ala Gly Lys Lys Thr Ala Phe Ser Ile Lys
    370                 375                 380

Leu Asp Tyr Val Lys Lys Pro Ile Pro Glu Thr Ala Met Val Lys Ile
385                 390                 395                 400

Leu Glu Lys Leu Tyr Glu Glu Asp Val Gly Ala Gly Val Leu Tyr Pro
                405                 410                 415

Tyr Gly Gly Ile Met Glu Glu Ile Ser Glu Ser Ala Ile Pro Phe Pro
                420                 425                 430

His Arg Ala Gly Ile Met Tyr Glu Leu Trp Tyr Thr Ala Ser Trp Glu
                435                 440                 445

Lys Gln Glu Asp Asn Glu Lys His Ile Asn Trp Val Arg Ser Val Tyr
        450                 455                 460

Asn Phe Thr Thr Pro Tyr Val Ser Gln Asn Pro Arg Leu Ala Tyr Leu
465                 470                 475                 480
```

Asn Tyr Arg Asp Leu Asp Leu Gly Lys Thr Asn His Ala Ser Pro Asn
            485                 490                 495

Asn Tyr Thr Gln Ala Arg Ile Trp Gly Glu Lys Tyr Phe Gly Lys Asn
        500                 505                 510

Phe Asn Arg Leu Val Lys Val Lys Thr Lys Val Asp Pro Asn Asn Phe
            515                 520                 525

Phe Arg Asn Glu Gln Ser Ile Pro Pro Leu Pro Pro His His His
        530                 535                 540

<210> SEQ ID NO 22
<211> LENGTH: 1635
<212> TYPE: DNA
<213> ORGANISM: Cannabis sp.

<400> SEQUENCE: 22

| | | |
|---|---|---|
| atgaattgct cagcattttc cttttggttt gtttgcaaaa taatattttt ctttctctca | 60 |
| ttcaatatcc aaatttcaat agctaatcct caagaaaact tccttaaatg cttctcggaa | 120 |
| tatattccta acaatccagc aaatccaaaa ttcatataca ctcaacacga ccaattgtat | 180 |
| atgtctgtcc tgaattcgac aatacaaaat cttagattca cctctgatac aaccccaaaa | 240 |
| ccactcgtta ttgtcactcc ttcaaatgtc tcccatatcc aggccagtat tctctgctcc | 300 |
| aagaaagttg gtttgcagat tcgaactcga agcggtggcc atgatgctga gggtttgtcc | 360 |
| tacatatctc aagtcccatt tgctatagta gacttgagaa acatgcatac ggtcaaagta | 420 |
| gatattcata gccaaactgc gtgggttgaa gccggagcta cccttggaga gtttattat | 480 |
| tggatcaatg agatgaatga gaattttagt tttcctggtg ggtattgccc tactgttggc | 540 |
| gtaggtggac actttagtgg aggaggctat ggagcattga tgcgaaatta tggccttgcg | 600 |
| gctgataata tcattgatgc acacttagtc aatgttgatg aaaagttct agatcgaaaa | 660 |
| tccatgggag aagatctatt tgggctata cgtggtggag gaggagaaaa ctttggaatc | 720 |
| attgcagcat ggaaaatcaa acttgttgtt gtcccatcaa aggctactat attcagtgtt | 780 |
| aaaaagaaca tggagataca tgggcttgtc aagttattta caaatggca aaatattgct | 840 |
| tacaagtatg acaaagattt aatgctcacg actcacttca gaactaggaa attacagat | 900 |
| aatcatggga agaataagac tacagtacat ggttacttct cttccatttt tcttggtgga | 960 |
| gtggatagtc tagttgactt gatgaacaag agctttcctg agttgggtat taaaaaaact | 1020 |
| gattgcaaag aattgagctg gattgataca accatcttct acagtggtgt tgtaaattac | 1080 |
| aacactgcta ttttaaaaa ggaaattttg cttgatagat cagctgggaa gaagacggct | 1140 |
| ttctcaatta gttagacta tgttaagaaa ctaatacctg aaactgcaat ggtcaaaatt | 1200 |
| ttggaaaaat tatatgaaga agaggtagga gttgggatgt atgtgttgta cccttacggt | 1260 |
| ggtataatgg atgagatttc agaatcagca attccattcc ctcatcgagc tggaataatg | 1320 |
| tatgaacttt ggtacactgc tacctgggag aagcaagaag ataacgaaaa gcatataaac | 1380 |
| tgggttcgaa gtgtttataa tttcacaact ccttatgtgt cccaaaatcc aagattggcg | 1440 |
| tatctcaatt atagggacct tgatttagga aaaactaatc ctgagagtcc taataattac | 1500 |
| acacaagcac gtatttgggg tgaaaagtat tttggtaaaa attttaacag gttagttaag | 1560 |
| gtgaaaacca aagctgatcc caataatttt tttagaaacg aacaaagtat cccacctctt | 1620 |
| ccaccgcatc atcat | 1635 |

<210> SEQ ID NO 23
<211> LENGTH: 96

```
<212> TYPE: DNA
<213> ORGANISM: Cannabis sp.

<400> SEQUENCE: 23
tatttttctt tctctcattc aatatccaaa cttcaattgc taatcctcga atgtaacaaa      60
tctaaaactt acacccaaaa caaccaattg tatatg                                96

<210> SEQ ID NO 24
<211> LENGTH: 100
<212> TYPE: DNA
<213> ORGANISM: Cannabis sp.

<400> SEQUENCE: 24
tatttttctt tttctcattc aatatccaaa cttccattgc taatcctcga atgcaacaaa      60
tctaaaactc gtatacactc aaaacaaccc attgtatatg                           100

<210> SEQ ID NO 25
<211> LENGTH: 100
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (70)..(73)
<223> OTHER INFORMATION: Deletion region

<400> SEQUENCE: 25
tatttttctt tytctcattc aatatccaaa cttcmattgc taatcctcga atgyaacaaa      60
tctaaaactc gtatacacyc aaaacaaccm attgtatatg                           100

<210> SEQ ID NO 26
<211> LENGTH: 10
<212> TYPE: DNA
<213> ORGANISM: Artificial Sequence
<220> FEATURE:
<223> OTHER INFORMATION: Synthetic primer

<400> SEQUENCE: 26 gtttttttgtt                                                            10

<210> SEQ ID NO 27
<211> LENGTH: 23
<212> TYPE: DNA
<213> ORGANISM: Artificial Sequence
<220> FEATURE:
<223> OTHER INFORMATION: Synthetic primer

<400> SEQUENCE: 27
atgcttctcg caatatattc cca                                              23
```

METHODS AND KITS FOR CLASSIFYING CANNABINOID PRODUCTION IN CANNABIS PLANTS

CROSS-REFERENCE TO RELATED APPLICATION

This application is a divisional of U.S. application Ser. No. 16/221,171, filed Dec. 14, 2018, which claims the benefit of priority of U.S. Provisional Application No. 62/598,967, filed Dec. 14, 2017, all of which is incorporated herein by reference in its entirety. The present application contains a Sequence Listing that has been submitted electronically in ASCII format and is hereby incorporated by reference in its entirety. The ASCII copy, created on Jun. 14, 2021, is named Sequence Listing ST25.txt and is 30,081 bytes in size.

BACKGROUND

*C. sativa* is an annual herbaceous flowering plant that has been cultivated throughout recorded history for use as fiber, seed oil, food, medicine and recreation. Cannabinoids are secondary metabolites found in *C. sativa* plants that can act on cannabinoid receptors in cells that alter neurotransmitter release in the brain. More than 100 cannabinoids have been isolated from *C. sativa*, which have varied effects on mammals to which they have been administered.

SUMMARY

The present disclosure encompasses the recognition that certain genotypes are associated with altered cannabinoid synthesis or an altered cannabinoid profile. For example, the present disclosure recognizes that certain variants (e.g., wild-type and/or mutated) of tetrahydrocannabinolic acid (THCA) synthase gene sequences and/or cannabidiolic acid (CBDA) synthase gene sequences can provide insight regarding synthesis of tetrahydrocannabinol (THC) and/or cannabidiol (CBD) in a *Cannabis* plant. The present disclosure provides a classification system for *Cannabis*, which designates a *Cannabis* plant as being of a particular type based on its genotype, which includes the classifications illustrated in FIG. 2 and outlined in Table 1 below:

TABLE 1

| CBDA Genotype | THCA Genotype | Classification |
| --- | --- | --- |
| CBDA$^-$/CBDA$^-$ | THCA$^+$/THCA$^+$ | Type Ia Plant |
| CBDA$^-$/CBDA$^-$ | THCA$^+$/THCA$^-$ | Type Ib Plant |
| CBDA$^+$/CBDA$^-$ | THCA$^+$/THCA$^+$ | Type IIa Plant |
| CBDA$^+$/CBDA$^-$ | THCA$^+$/THCA$^-$ | Type IIb Plant |
| CBDA$^+$/CBDA$^+$ | THCA$^+$/THCA$^+$ | Type IIb Plant |
| CBDA$^+$/CBDA$^+$ | THCA$^+$/THCA$^-$ | Type IIc Plant |
| CBDA$^+$/CBDA$^-$ | THCA$^-$/THCA$^-$ | Type IIIa Plant |
| CBDA$^+$/CBDA$^+$ | THCA$^-$/THCA$^-$ | Type IIIb Plant |
| CBDA$^-$/CBDA$^-$ | THCA$^-$/THCA$^-$ | Type IV Plant |

Such a classification system can be utilized, e.g., in the selection of a *Cannabis* plant for various purposes. For example, a Type IIIb *Cannabis* plant (CBDA$^+$/CBDA$^+$ and THCA$^-$/THCA$^-$) may be useful as a therapeutic, particularly in applications in which psychoactive effects caused by THC are undesirable. The present disclosure also recognizes Type V *Cannabis* plants. In some embodiments, a Type V *Cannabis* plant is characterized by a mutation in one or both of a olivetol synthase gene sequence and a divarinic acid synthase gene sequence. Olivetolic acid and divarinic acid are produced by enzymes olivetol synthase and divarinic acid synthase, respectively, in the cannabinoid synthesis pathway (see, e.g., FIG. 1, panel (A)).

The present disclosure further recognizes certain limits associated with previous assays to characterize THCA synthase, e.g., an inability to detect a THCA synthase gene sequence (e.g., because assays use primers or probes are complementary to highly variant sequences), and/or a false-positive detection (e.g., by amplification of a THCA synthase pseudogene). The present disclosure provides a method that reliably and accurately detects a THCA synthase gene sequence in a *Cannabis* plant. The present disclosure provides the insight that detection of a THCA synthase gene sequence (e.g., a wild-type or mutated THCA synthase gene sequence) present in a *Cannabis* plant can be achieved by amplification of a THCA synthase gene sequence using one or more primers with sequences complementary to sequences (e.g., promoter) upstream of the coding sequence and (e.g., terminator region, 5' UTR, etc.) downstream of the coding sequence may be particularly useful for in vitro detection of a functional THCA synthase gene sequence. Moreover, the present disclosure provides methods that include detection of a wild-type THCA synthase gene sequence and a mutant version of a THCA synthase gene sequence, thereby indicating the THCA synthase genotype of the plant.

The present disclosure also provides a method that reliably and accurately detects a CBDA synthase gene sequence in a *Cannabis* plant. The present disclosure provides methods that include detection of a wild-type CBDA synthase gene sequence and a mutant version of a CBDA synthase gene sequence, thereby indicating the CBDA synthase genotype of the plant. In some embodiments, detection of a wild-type CBDA synthase gene sequence in a *Cannabis* plant can be achieved by amplification of a CBDA synthase gene sequence using a primer that is complementary (at least in part) to a sequence of a first CBDA synthase gene sequence (e.g., CGTA at residues 330-333 in FIG. 4). In some embodiments, detection of a mutant CBDA synthase gene sequence in a *Cannabis* plant can be achieved by amplification of a CBDA synthase gene sequence using a primer that is complementary (at least in part) to a CBDA synthase gene sequence that includes a deletion of the first sequence (e.g., ACTTAC at residues 327-329 and 334-336 in FIG. 4).

In some aspects, the present disclosure relates to methods and kits for classifying cannabinoid production in a *Cannabis* plant, such as a *C. sativa* plant, a *C. indica* plant, or a *C. ruderalis* plant.

In some aspects, the present disclosure provides methods that include detection of one or more nucleic acid sequences in a sample of a *Cannabis* plant. In some embodiments, a method includes detecting the presence of a tetrahydrocannabinolic acid (THCA) synthase gene sequence, e.g., a THCA synthase gene sequence comprising a THCA synthase coding region (e.g., an entire THCA synthase coding region) and/or a THCA synthase gene sequence promoter. In some embodiments, a method includes detecting the presence of a mutated THCA synthase gene sequence. In some embodiments, a mutated THCA synthase gene sequence includes at least one mutation that alters the activity of a THCA synthase encoded by the mutated THCA synthase gene sequence relative to a THCA synthase encoded by a wild-type THCA synthase gene sequence. In some embodiments, a method includes detecting the presence of a wild-type cannabidiolic acid (CBDA$^{wt}$) synthase gene sequence. In some embodiments, a method includes detecting the presence of a mutated cannabidiolic acid (CBDA$^{mut}$) synthase gene sequence. In some embodiments, a mutated CBDA synthase gene sequence comprises a deletion mutation.

In some embodiments, a method includes detecting a wild-type THCA synthase gene sequence, a mutant THCA synthase gene sequence, a wild-type CBDA synthase gene sequence, a mutant CBDA synthase gene sequence, or any combination thereof from a sample that comprises *Cannabis* nucleic acid (i.e., nucleic acid of a *Cannabis* plant). In some embodiments, a method further includes detecting one, two, three, four, or more of a wild-type olivetol synthase gene sequence, a variant olivetol synthase gene sequence, a wild-type divarinic acid synthase gene sequence, a variant divarinic acid synthase gene sequence, a wild-type limonene synthase gene sequence, and a variant limonene synthase gene sequence from a sample that comprises *Cannabis* nucleic acid.

In some embodiments, detection of one or more nucleic acid sequences in a sample of *Cannabis* plant includes isothermic nucleic acid amplification. In some embodiments, isothermic nucleic acid amplification is a Loop-Mediated Isothermal Amplification (LAMP) assay. In some embodiments, a LAMP assay is a colorimetric LAMP assay.

In some embodiments, detection of a THCA synthase gene sequence includes amplification of a THCA synthase gene sequence that is at least 2000 nucleotides long. In some certain embodiments, an amplified THCA synthase gene sequences is 1500-2500, 1750-2250, 2000-2200, or 2100-2200 nucleotides long. In some embodiments, an amplified THCA synthase gene sequence includes at least part of the THCA synthase promoter and 5' UTR.

In some embodiments, a *Cannabis* plant is a *C. sativa* plant. In some embodiments, a *Cannabis* plant is a *C. indica* plant. In some embodiments, a *Cannabis* plant is a *C. ruderalis* plant.

In some embodiments, detecting the presence of a THCA synthase gene sequence includes contacting a sample that comprises nucleic acid from the *Cannabis* plant with at least two THCA synthase primers under conditions sufficient for amplification of a THCA synthase gene sequence. In some certain embodiments, detecting the presence of a THCA synthase gene sequence includes contacting nucleic acid from a *Cannabis* plant with at least two primers that are at least 70%, 75%, 80%, 85%, 85%, 87%, 88%, 89%, 90%, 91%, 92%, 93%, 94%, 95%, 96%, 97%, 98%, 99%, or 100% identical to any of SEQ ID NOs: 8-12.

In some certain embodiments, detecting the presence of a THCA synthase gene sequence is by LAMP amplification and includes contacting nucleic acid from a *Cannabis* plant with four or more primers that are at least 70%, 75%, 80%, 85%, 85%, 87%, 88%, 89%, 90%, 91%, 92%, 93%, 94%, 95%, 96%, 97%, 98%, 99%, or 100% identical to any of SEQ ID NOs: 8-12.

In some embodiments, detecting the presence of a mutated THCA synthase gene sequence includes contacting a sample that comprises nucleic acid from the *Cannabis* plant with at least two THCA synthase primers under conditions sufficient for amplification of a mutated THCA synthase gene sequence.

In some embodiments, detecting the presence of a wild-type cannabidiolic acid (CBDA$^{WT}$) synthase gene sequence includes contacting a sample that comprises nucleic acid from the *Cannabis* plant with at least two CBDA synthase primers under conditions sufficient for amplification of a wild-type CBDA (CBDA$^{WT}$) synthase gene sequence. In some certain embodiments, detecting the presence of a CBDA$^{WT}$ synthase gene sequence includes contacting nucleic acid from a *Cannabis* plant with at least two primers that are at least 70%, 75%, 80%, 85%, 85%, 87%, 88%, 89%, 90%, 91%, 92%, 93%, 94%, 95%, 96%, 97%, 98%, 99%, or 100% identical to any of SEQ ID NOs: 13-18 and 27.

In some embodiments, detecting the presence of a mutated cannabidiolic acid (CBDA$^{mut}$) synthase gene sequence includes contacting a sample that comprises nucleic acid from the *Cannabis* plant with at least two CBDA synthase primers under conditions sufficient for amplification of a CBDA$^{mut}$ synthase gene sequence. In some embodiments a CBDA$^{mut}$ synthase is a deletion (CBDA$^{del}$). In some certain embodiments, detecting the presence of a CBDA$^{del}$ synthase gene sequence includes contacting nucleic acid from a *Cannabis* plant with at least two primers that are at least 70%, 75%, 80%, 85%, 85%, 87%, 88%, 89%, 90%, 91%, 92%, 93%, 94%, 95%, 96%, 97%, 98%, 99%, or 100% identical to any of SEQ ID NOs: 13, 15-19, and 27.

In some embodiments, detecting the presence of a THCA synthase gene sequence includes contacting a sample that comprises nucleic acid from the *Cannabis* plant with at least five THCA synthase primers under conditions sufficient for LAMP of a THCA synthase gene sequence. In some certain embodiments, the at least five primer sequences are at least 70%, 75%, 80%, 85%, 85%, 87%, 88%, 89%, 90%, 91%, 92%, 93%, 94%, 95%, 96%, 97%, 98%, 99%, or 100% identical to each of SEQ ID NOs: 8-12.

In some embodiments, detecting the presence of a mutated THCA synthase gene sequence includes contacting a sample that comprises nucleic acid from the *Cannabis* plant with at least five THCA synthase primers under conditions sufficient for LAMP of a mutated THCA synthase gene sequence.

In some embodiments, detecting the presence of a wild-type cannabidiolic acid (CBDA$^{WT}$) synthase gene sequence includes contacting a sample that comprises nucleic acid from the *Cannabis* plant with at least five CBDA synthase primers under conditions sufficient for LAMP of a CBDA$^{WT}$ synthase gene sequence. In some certain embodiments, detecting the presence of a CBDA$^{WT}$ synthase gene sequence is by LAMP amplification and includes contacting nucleic acid from a *Cannabis* plant with six primers that are at least 70%, 75%, 80%, 85%, 85%, 87%, 88%, 89%, 90%, 91%, 92%, 93%, 94%, 95%, 96%, 97%, 98%, 99%, or 100% identical to each of SEQ ID NOs: 13-18 and 27.

In some embodiments, detecting the presence of a mutated cannabidiolic acid (CBDA$^{mut}$) synthase gene sequence includes contacting a sample that comprises nucleic acid from the *Cannabis* plant with at least five CBDA synthase primers under conditions sufficient for LAMP of a CBDA$^{mut}$ synthase gene sequence. In some embodiments a CBDA$^{mut}$ synthase is a deletion (CBDA$^{del}$). In some certain embodiments, detecting the presence of a CBDA$^{del}$ synthase gene sequence is by LAMP amplification and includes contacting nucleic acid from a *Cannabis* plant with six primers that are at least 70%, 75%, 80%, 85%, 85%, 87%, 88%, 89%, 90%, 91%, 92%, 93%, 94%, 95%, 96%, 97%, 98%, 99%, or 100% identical to each of SEQ ID NOs: 13, 15-19, and 27.

In some embodiments, a method of the present disclosure includes a step of analyzing results from one or more detecting steps, thereby characterizing a *Cannabis* plant as a Type Ia, Type Ib, Type IIa, Type IIb, Type IIc, Type IIIa, Type IIIb, Type IV or Type V plant.

In some aspects, the present disclosure provides methods that include contacting a sample that comprises nucleic acid from a *Cannabis* plant with at least two primers sufficient for amplification of a *Cannabis* enzyme gene sequence. In some embodiments, a method includes contacting a sample that comprises nucleic acid from a *Cannabis* plant with at least two primers sufficient for amplification of a THCA synthase gene sequence under conditions sufficient for amplification of a THCA synthase gene sequence, where at least two THCA synthase primers include a forward THCA synthase primer and a reverse THCA synthase primer. In some embodiments, a forward THCA synthase primer is complementary to a sequence that is 200-1000 nucleotides upstream of a THCA synthase open reading frame in a *Cannabis* genome. In some embodiments, a reverse THCA synthase primer is complementary to a sequence that is 50-1000 nucleotides downstream of the THCA synthase open reading frame.

In some embodiments, a method includes contacting a sample that comprises nucleic acid from the *Cannabis* plant with at least two cannabidiolic acid (CBDA) synthase primers under conditions sufficient for amplification of a Bd variant of CBDA synthase ($CBDA^{Bd}$) gene sequence. In some embodiments, at least one $CBDA^{Bd}$ synthase primer is complementary to a sequence that bridges a 4 nucleotide deletion found in the $CBDA^{Bd}$ open reading frame.

In some embodiments, a method includes contacting a sample that comprises nucleic acid from the *Cannabis* plant with at least two cannabidiolic acid (CBDA) synthase primers under conditions sufficient for amplification of a wild-type CBDA ($CBDA^{WT}$) synthase gene sequence. In some embodiments, at least one $CBDA^{WT}$ synthase primer is complementary to a sequence that includes the 4 nucleotide deleted in the $CBDA^{Bd}$ synthase open reading frame.

In some embodiments, a method includes a combination of steps that include contacting a sample that comprises nucleic acid from the *Cannabis* plant with primers under conditions sufficient for amplification of two or more of a THCA synthase gene sequence, a variant THCA synthase gene sequence, a $CBDA^{WT}$, synthase gene sequence, and/or a $CBDA^{mut}$ synthase gene sequence.

In some embodiments, a method includes amplification of THCA synthase gene sequence that is at least 2000 nucleotide long. In some certain embodiments, an amplified THCA synthase gene sequences is 1500-2500, 1750-2250, 2000-2200, or 2100-2200 nucleotides long. In some embodiments, an amplified THCA synthase gene sequence includes at least part of the THCA synthase promoter and 5' UTR.

In some embodiments, amplification of one or more nucleic acid sequences in a *Cannabis* genome is by isothermic nucleic acid amplification. In some embodiments, amplification includes performing a Loop-Mediated Isothermal Amplification (LAMP) assay. In some embodiments, a LAMP assay is a colorimetric assay.

In some embodiments, a *Cannabis* plant is a *C. sativa* plant. In some embodiments, a *Cannabis* plant is a *C. indica* plant. In some embodiments, a *Cannabis* plant is a *C. ruderalis* plant.

In some embodiments, amplification of a THCA synthase gene sequence includes contacting a sample that comprises nucleic acid from the *Cannabis* plant with at least five THCA synthase primers under conditions sufficient for LAMP of a THCA synthase gene sequence. In some certain embodiments, the at least five primer sequences are at least 70%, 75%, 80%, 85%, 85%, 87%, 88%, 89%, 90%, 91%, 92%, 93%, 94%, 95%, 96%, 97%, 98%, 99%, or 100% identical to each of SEQ ID NOs: 8-12.

In some embodiments, amplification of a mutated THCA synthase gene sequence includes contacting a sample that comprises nucleic acid from the *Cannabis* plant with at least five THCA synthase primers under conditions sufficient for LAMP of a mutated THCA synthase gene sequence.

In some embodiments, amplification of a wild-type cannabidiolic acid ($CBDA^{WT}$) synthase gene sequence includes contacting a sample that comprises nucleic acid from the *Cannabis* plant with at least five CBDA synthase primers under conditions sufficient for LAMP of a wild-type CBDA ($CBDA^{WT}$) synthase gene sequence. In some certain embodiments, detecting the presence of a $CBDA^{WT}$ synthase gene sequence is by LAMP amplification and includes contacting nucleic acid from a *Cannabis* plant with six primers that are at least 70%, 75%, 80%, 85%, 85%, 87%, 88%, 89%, 90%, 91%, 92%, 93%, 94%, 95%, 96%, 97%, 98%, 99%, or 100% identical to each of SEQ ID NOs: 13-18 and 27.

In some embodiments, amplification of a mutated cannabidiolic acid ($CBDA^{mut}$) synthase gene sequence includes contacting a sample that comprises nucleic acid from the *Cannabis* plant with at least five CBDA synthase primers under conditions sufficient for LAMP of a $CBDA^{mut}$ synthase gene sequence. In some embodiments a $CBDA^{mut}$ synthase is a deletion ($CBDA^{del}$). In some certain embodiments, detecting the presence of a $CBDA^{del}$ synthase gene sequence is by LAMP amplification and includes contacting nucleic acid from a *Cannabis* plant with six primers that are at least 70%, 75%, 80%, 85%, 85%, 87%, 88%, 89%, 90%, 91%, 92%, 93%, 94%, 95%, 96%, 97%, 98%, 99%, or 100% identical to each of SEQ ID NOs: 13, 15-19, and 27.

In some aspects, the present disclosure provides kits that include primers that are complementary to sequences encoding *Cannabis* enzymes that are involved in cannabinoid synthesis. In some embodiments, a kit may be used to amplify a genomic sequence form a *C. sativa, C. indica*, and/or a *C. ruderalis* plant.

In some embodiments, a kit includes at least two THCA synthase primers including a forward THCA synthase primer and a reverse THCA synthase primer, wherein the forward THCA synthase primer is complementary to a sequence that is 200-1000 nucleotides upstream of a THCA synthase open reading frame in a *Cannabis* genome and the reverse THCA synthase primer is complementary to a sequence that is 50-1000 nucleotides downstream of the THCA synthase open reading frame.

In some embodiments, a forward THCA synthase primer is or comprises a sequence complementary to 20-60 nucleotides of SEQ ID NO: 6 and wherein the reverse THCA synthase primer is or comprises a sequence complementary to 20-60 nucleotides of SEQ ID NO: 7. In some embodiments, a kit includes at least five THCA synthase primers.

In some embodiments, a kit of the present disclosure may additionally or alternatively include at least two cannabidiolic acid (CBDA) synthase primers for amplification of a Bd variant of CBDA synthase ($CBDA^{Bd}$) gene sequence and/or at least two cannabidiolic acid (CBDA) synthase primers for amplification of a wild-type CBDA ($CBDA^{WT}$) synthase gene sequence. In some embodiments, at least one $CBDA^{Bd}$ synthase primer is complementary to a sequence that bridges a 4 nucleotide deletion found in the $CBDA^{Bd}$ open reading frame. In some embodiments, at least one $CBDA^{WT}$ synthase primer is complementary to a sequence that includes the 4 nucleotides deleted in the $CBDA^{Bd}$ synthase open reading frame.

In some certain embodiments, at least one $CBDA^{WT}$ synthase primer is or comprises a sequence that is at least 80% identical to SEQ ID NO: 14. In some certain embodiments, at least one CBDA$^{Bd}$ synthase primer is or comprises a sequence that is at least 80% identical to SEQ ID NO: 19. In some certain embodiments, at least one CBDA$^{WT}$ synthase primer is or comprises a sequence of SEQ ID NO: 14. In some certain embodiments, at least one CBDA$^{Bd}$ synthase primer is or comprises a sequence of SEQ ID NO: 19.

In some embodiments, a kit of the present disclosure may additionally or alternatively include primers for amplification of one or more of a wild-type olivetol synthase gene sequence, a variant olivetol synthase gene sequence, a wild-type divarinic acid synthase gene sequence, a variant divarinic acid synthase gene sequence, a wild-type limonene synthase gene sequence, and a variant limonene synthase gene sequence from a sample that comprises *Cannabis* nucleic acid.

Any of the kits of the present disclosure may additionally include reagents for a Loop-Mediated Isothermal Amplication (LAMP) assay. In some embodiments, a LAMP assay is a colorimetric LAMP assay.

These, and other aspects encompassed by the present disclosure, are described in more detail below and in the claims.

BRIEF DESCRIPTION OF THE DRAWING

The Figures described below, that together make up the Drawing, are for illustration purposes only, not for limitation.

FIG. 1: Panels (A) and (B) provide schematic representations of portion of the cannabinoid synthesis pathway.

FIG. 4: depicts a position-specific weight matrix for alignment of CBDA synthase alleles (SEQ ID NOS: 23, 24, and 25) in a *Cannabis* plant.

FIG. 5: depicts isothermic (e.g., LAMP) amplification of a THCA synthase gene sequence. Panel (A) depicts an isothermic (e.g., LAMP) amplification at 65° C. of THCA synthase gene sequence with Kitamura primers ("K primers") (Kitamura et al., (2017) *Journal of natural medicines*, 71(1):86-95 and Kitamura et al., (2016) *Biological & pharmaceutical bulletin*, 39(7):1144-9, both of which are incorporated herein by reference) and Long Range primers ("LR primers") on the *Cannabis* strain Granddaddy Purple ("GDP"). Additionally, an isothermic amplification with K primers of various strains of *Cannabis*: Otto, two hemp samples, Grape Stomper (RSP10516), and Erk Train X Deadhead OG (RSP10517) were also determined. Panel (B) depicts an isothermic (LAMP) amplification with LR primers at various temperatures for multiple strains of *Cannabis*.

FIG. 6: depicts an isothermic (LAMP) amplification of THCA gene sequence at 65° C. with Long Range primers on various *Cannabis* strains.

FIG. 9: depicts exemplary primer sequences (SEQ ID NOS: 8, 9, 10, 11, 12, 13, 14, 15, 16, 17, 18, 13, 19, 15, 16, 17, and 18 in that order) useful in the context of the present disclosure.

FIG. 10: depicts a table of exemplary THCA synthase gene sequence.

CERTAIN DEFINITIONS

Figure 2:
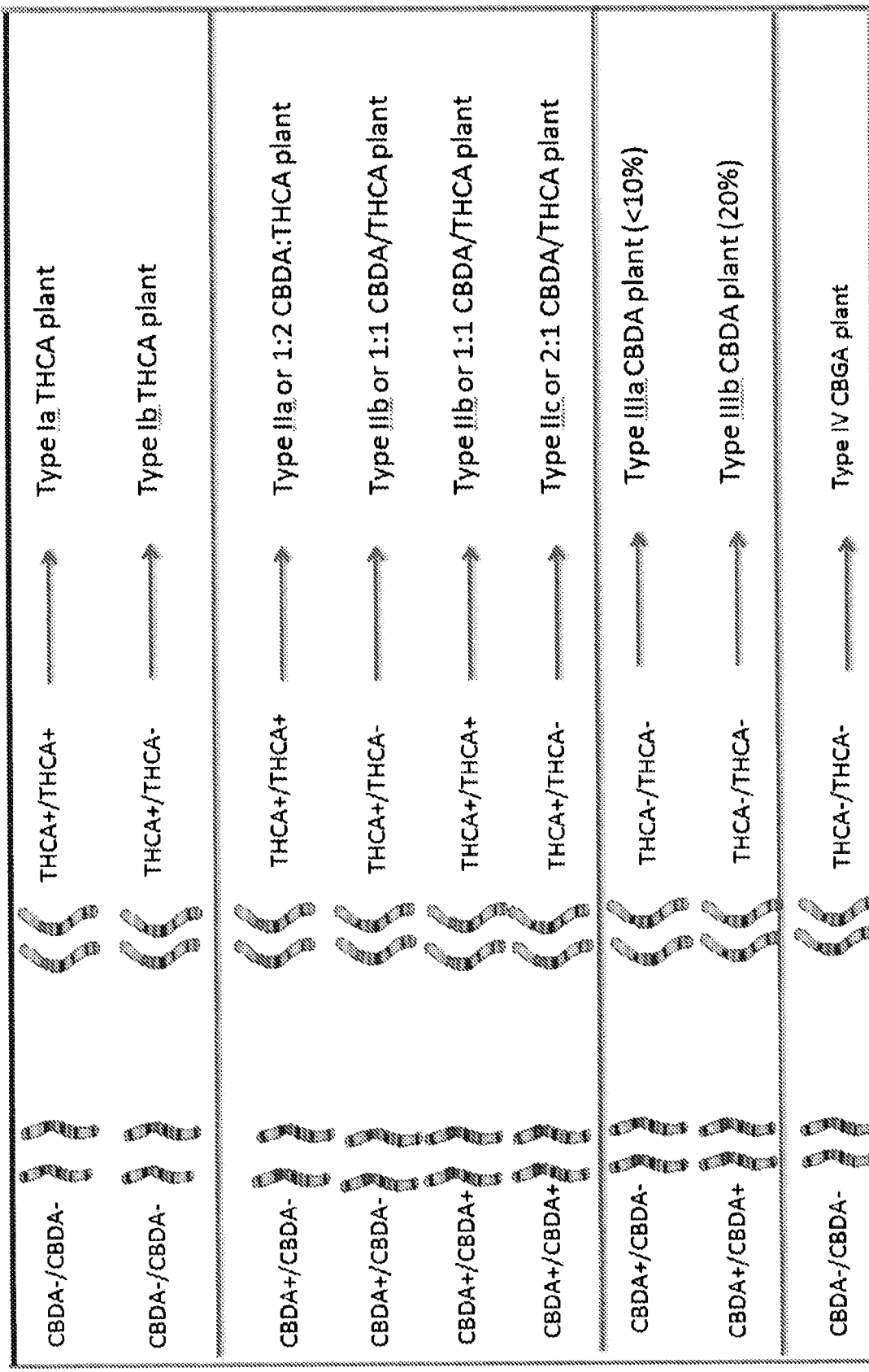
FIG. 2: depicts a subtype classification system for *Cannabis* plants.

Associated With: The term "associated with" is used herein to describe an observed correlation between two items or events. For example, a mutation in THCA synthase may be considered to be "associated with" a particular cannabinoid synthesis profile and/or cannabinoid composition.

*Cannabis*: As used herein, "*Cannabis*" refers to any plant in the genus *Cannabis*. In some embodiments, "*Cannabis*" refers to a part of, a specific compound from, and/or any product from a *Cannabis* plant (e.g., *C. sativa, C. indica, C. ruderalis*). For example, a "*Cannabis* enzyme" refers to an enzyme from a *Cannabis* plant. Similarly, a "*Cannabis* genome" refers to a genome from a *Cannabis* plant. *Cannabis* includes both "marijuana" and "hemp," two forms of *Cannabis* that are distinguished on the basis of the relative abundances of different cannabinoids. *Cannabis* includes any variety of *Cannabis* species, cultivar of *Cannabis* species, or hybrid between any *Cannabis* species.

Chemotype: As used herein, the term "chemotype" refers to chemically distinct entity (e.g., plant) with a particular profile of metabolites. In some embodiments, a chemotype is a particular type of *Cannabis* plant with a particular profile of one or more cannabinoids. In some embodiments, plants having different chemotypes may have same or different morphological characteristics. In some embodiments, a chemotype is characterized by a highly abundant chemical produced by that entity (e.g., plant). In some certain embodiments, a chemotype may refer to a *Cannabis* plant with an abundance of one or more cannabinoids (e.g., THC or CBD). In some embodiments, abundance of one or more cannabinoids may be a relative amount (e.g., a ratio of cannabinoids, such as a THC:CBD ratio).

Coding sequence: As used herein, the term "coding sequence" refers to a sequence of a nucleic acid or its complement, or a part thereof, that (i) can be transcribed to an mRNA sequence that can be translated to produce a polypeptide or a fragment thereof, or (ii) an mRNA sequence that can be translated to produce a polypeptide or a fragment thereof. Coding sequences include exons in genomic DNA or immature primary RNA transcripts, which are joined together by the cell's biochemical machinery to provide a mature mRNA.

Gene and Gene sequence: The term "gene," as used herein, refers to a part of the genome that codes for a product (e.g., an RNA product and/or a polypeptide product). A "gene sequence" is a sequence that includes at least a portion of a gene (e.g., all or part of a gene) and/or regulatory elements associated with a gene. In some embodiments, a gene includes coding sequence; in some embodiments, a gene includes non-coding sequence. In some particular embodiments, a gene may include both coding (e.g., exonic) and non-coding (e.g., intronic) sequences. In some embodiments, a gene may include one or more regulatory elements (e.g., a promoter) that, for example, may control or impact one or more aspects of gene expression (e.g., cell-type-specific expression, inducible expression, etc.).

Mutation: As used herein, the term "mutation" refers to a change introduced into a parental sequence, including, but not limited to, substitutions, insertions, deletions (including truncations). The consequences of a mutation include, but are not limited to, the creation of a new character, property, function, phenotype or trait not found in the protein encoded by the parental sequence, or the increase or reduction/ elimination of an existing character, property, function, phenotype or trait not found in the protein encoded by the parental sequence.

Nucleic Acid: As used herein, the terms "nucleic acid," "nucleic acid molecule," "oligonucleotide," and "polynucleotide" are each used herein to refer to a polymer of at least three nucleotides. In some embodiments, a nucleic acid comprises deoxyribonucleic acid (DNA). In some embodiments comprises ribonucleic acid (RNA). In some embodiments, a nucleic acid is single stranded. In some embodiments, a nucleic acid is double stranded. In some embodiments, a nucleic acid comprises both single and double stranded portions. Unless otherwise stated, the terms encompass nucleic acid-like structures with synthetic backbones, as well as amplification products. In some embodiments, nucleic acids of the present disclosure are linear nucleic acids.

Plant part: As used herein, the term "plant part" refers to any part of a plant including but not limited to the embryo, shoot, root, stem, seed, stipule, leaf, petal, flower bud, flower, ovule, bract, trichome, branch, petiole, internode, bark, pubescence, tiller, rhizome, frond, blade, ovule, pollen, stamen, and the like. The two main parts of plants grown in some sort of media, such as soil or vermiculite, are often referred to as the "above-ground" part, also often referred to as the "shoots", and the "below-ground" part, also often referred to as the "roots." Plant part may also include certain extracts such as kief or hash which includes *cannabis* trichomes or glands.

Primer: The terms "primer," as used herein, typically refers to oligonucleotides that hybridize in a sequence specific manner to a complementary nucleic acid molecule (e.g., a nucleic acid molecule comprising a target sequence). In some embodiments, a primer will comprise a region of nucleotide sequence that hybridizes to at least 8, e.g., at least 10, at least 15, at least 20, at least 25, or 20 to 60 nucleotides of a target nucleic acid (i.e., will hybridize to a sequence of the target nucleic acid). In general, a primer sequence is identified as being either "complementary" (i.e., complementary to the coding or sense strand (+)), or "reverse complementary" (i.e., complementary to the anti-sense strand (−)). In some embodiments, the term "primer" may refer to an oligonucleotide that acts as a point of initiation of a template-directed synthesis using methods such as PCR (polymerase chain reaction) under appropriate conditions (e.g., in the presence of four different nucleotide triphosphates and a polymerization agent, such as DNA polymerase in an appropriate buffer solution containing any necessary reagents and at suitable temperature(s)). Such a template directed synthesis is also called "primer extension." For example, a primer pair may be designed to amplify a region of DNA using PCR. Such a pair will include a "forward primer" and a "reverse primer" that hybridize to complementary strands of a DNA molecule and that delimit a region to be synthesized and/or amplified.

Reference: As will be understood from context, a reference sequence, sample, population, agent or individual is one that is sufficiently similar to a particular sequence, sample, population, agent or individual of interest to permit a relevant comparison (i.e., to be comparable). In some embodiments, information about a reference sample is obtained simultaneously with information about a particular sample. In some embodiments, information about a reference sample is historical. In some embodiments, information about a reference sample is stored for example in a computer-readable medium. In some embodiments, comparison of a particular sample of interest with a reference sample establishes identity with, similarity to, or difference of a particular sample of interest relative to a reference.

Regulatory Sequence: The term "regulatory sequence" is intended to include promoters, enhancers and other expression control elements (e.g., polyadenylation signals).

Wild type: As used herein, the term "wild-type" refers to a typical or common form existing in nature; in some embodiments it is the most common form.

DETAILED DESCRIPTION OF CERTAIN EMBODIMENTS

The disclosure provides useful methods for characterizing certain genetic sequences of *Cannabis* plants. The present disclosure encompasses a recognition that amplification of a region of THCA synthase gene sequence that includes a THCA synthase gene sequence promoter and/or termination region can robustly predict the presence of a functional THCA synthase gene sequence. The present disclosure also provides a method that reliably and accurately detects a CBDA synthase gene sequence in a *Cannabis* plant. Methods of the present disclosure may include characterization (e.g., detection, amplification) of CDBA gene sequences, including wildtype ($CDBA^{wt}$) and deletion ($CDBA^{del}$) sequences.

*Cannabis* Plants and Cannabinoids

Two sub-species of *Cannabis* plants are *C. indica* and *C. sativa*, which are commonly distinguished based on morphology of a *Cannabis* plant. Generally, *C. sativa* plants are taller, loosely branched and have long, narrow leaves, while *C. indica* plants are shorter, more densely branched and have wider leaves. However, there is some doubt about the accuracy of these generalizations. Originally, classification of *C. indica* was made in 1785 by a French biologist named Jean-Baptiste Lamarck who observed that certain marijuana plants from India were intoxicating and could be made into hashish. In contrast, traditional hemp crops in Europe had little or no mind-altering effect. Lamark came up with the name *C. indica* to distinguish Indian *Cannabis* from European hemp, which was known at the time as *C. sativa*. Therefore, additionally or alternatively, *Cannabis* plants can be characterized by production of one or more chemical metabolites (e.g., cannabinoids). In some embodiments, a *Cannabis* plant is characterized as having a specified level (e.g., high/low) of one or more cannabinoids, flavonoids and/or terpenes.

Cannabinoids are terpenophenolic secondary metabolites, produced by *Cannabis* plants in the sessile and stalked trichomes. Trichomes are generally abundant on the inflorescences of a *Cannabis* plant, present in lower number on leaves, petioles and stems, and generally absent on roots and seeds. As a consequence, roots and seeds generally do not contain cannabinoids. In some embodiments, a *Cannabis* plant for use in a method of the present disclosure may include any plant part, such as, for example, a bloom, leaf, petiole, stem, root and/or seed.

As an annual, *Cannabis* plants follow a solar cycle consisting of two basic stages often referred to as vegetative, and bloom (flowering). Cannabinoid synthesis occurs predominantly in bloom (flowering) phase. In some embodiments, a *Cannabis* plant for use in a method of the present disclosure is in a vegetative state. In some embodiments, a *Cannabis* plant for use in a method of the present disclosure is in a flowering state.

Cannabinoids such as, for example, delta-9-tetrahydrocannabinol (Δ9-THC or THC), cannabidiol (CBD), cannabinol (CBN), cannabigerol (CBG), and cannabichromene (CBC) have been identified from *Cannabis* plants. In some embodiments, a cannabinoid is an aryl-substituted monoterpene. Generally, cannabinoids are lipid soluble and neutral. Cannabinoids can be divided into at least ten classes: cannabigerol, cannabichromene, cannabidiol, delta-9-tetrahydrocannabinol, delta-8-tetrahydrocannabinol, cannabicyclol, cannabielsoin, cannabinol and cannabinodiol, cannabitriol and miscellaneous cannabinoids.

In some embodiments, *C. indica* plants are characterized as having high THC:CBD ratios and *C. sativa* plants are characterized as having high CBD:THC ratios. However, many strains produce varying amounts of cannabinoids, which may be due to hybridization, or cross breeding. Accordingly, in some embodiments, a *C. sativa* plant may be rich in THC and a *C. indica* plant may have low THC.

*Cannabis* plants for use in accordance with the methods of the present disclosure may be, for example, a *C. sativa* plant and/or a *C. indica* plant. In some embodiments, a *Cannabis* plant may be characterized as and/or determined to be rich in one or more cannabinoids such as a cannabigerol, cannabichromene, cannabidiol, delta-9-tetrahydrocannabinol, delta-8-tetrahydrocannabinol, cannabicyclol, cannabielsoin, cannabinol and cannabinodiol, and/or cannabitriol. In some embodiments, a *Cannabis* plant is determined to be or characterized as rich in THC. In some embodiments, a *Cannabis* plant is determined to be or characterized as rich in CBD.

In some embodiments, a *Cannabis* plant may be characterized as and/or determined to be expressing a low amount of one or more cannabinoids such as a cannabigerol, cannabichromene, cannabidiol, delta-9-tetrahydrocannabinol, delta-8-tetrahydrocannabinol, cannabicyclol, cannabielsoin, cannabinol and cannabinodiol, and/or cannabitriol. In some embodiments, a *Cannabis* plant is determined to be or characterized as low in THC. In some embodiments, a *Cannabis* plant is determined to be or characterized as low in CBD.

The present disclosure also encompasses the recognition that levels of two or more cannabinoids may be related. FIG. 1 depict portions of the cannabinoid synthesis pathway. As shown in FIG. 1, Panels A and B, cannabigerolic acid is a precursor of both THCA and CBDA. THCA and CBDA each undergo non-enzymatic conversion to THC and CBD, respectively. Since both THC and CBD are synthesized from the same precursor, increased synthesis of one of these compounds may reduce synthesis of the other (e.g., by depletion of precursor). In some embodiments, the rate/amount of THC synthesis is inversely proportional to the rate/amount of CBD synthesis. Moreover, as synthesis of both THC and CBD use cannabigerolic acid, increased synthesis of either or both of these cannabinoids may reduce the amount of cannabigerolic acid. In some embodiments, the rate/amount of THC synthesis is inversely proportional to the rate/amount of cannabigerolic acid. In some embodiments, the rate/amount of CBD synthesis is inversely proportional to the rate/amount of cannabigerolic acid.

Earlier studies proposed a model that the genes coding for functional THCA- and CBDA-synthase (referred to as Bt and Bd, respectively) are allelic and codominant. (de Meijer et al. (2003) *Genetics*, 163(1):335-46, PMID: 12586720, which is incorporated herein by reference). Variations in CBDA/THCA ratios could be directly related to a differential efficiency in transforming cannabigerolic acid by THCA- and CBDA-synthases. Id.

In some embodiments, a *Cannabis* plant genome includes a THCA synthase gene sequence. In some embodiments, a *Cannabis* plant genome includes a wild-type THCA synthase gene sequence. In some embodiments, a *Cannabis* plant genome is homozygous for a wild-type THCA synthase gene sequence. In some embodiments, a *Cannabis* plant genome is heterozygous for a wild-type THCA synthase gene sequence. In some embodiments, a *Cannabis* plant genome is homozygous for a variant THCA synthase gene sequence. In some embodiments, a *Cannabis* plant genome is heterozygous for a variant THCA synthase gene sequence. In some embodiments, a *Cannabis* plant genome includes a THCA synthase gene sequence that is or comprises a sequence that is 70%, 75%, 80%, 85%, 85%, 87%, 88%, 89%, 90%, 91%, 92%, 93%, 94%, 95%, 96%, 97%, 98%, 99%, or 100% identical to SEQ ID NO: 1, or a portion thereof.

```
Exemplary C. sativa THCA synthase gene sequence
                                         SEQ ID NO: 1
ATGGGAACCATAATAAACTATAAAAGTCATTATGTGTACTTGCTACCAT

AGGCACCTATATCCCACAAACTAGCTACCATAGCCAATTTCTTTTTTGT

TTCCAATATCCAATTTTTATTGATGCCAAACTATTCAATGTACAATGTA

CATTTATTTTCAATAAGGGCTTCACCTAACAAAGGTGCCTAATTTTAGT

TGATTTATTTTTTATCACATGTGACTATTTAATGACTATCAAATTATAA

AATATTTAAGTCAATTTATTTTGCCCCAACTCCAATATATAATATTATAA

ATAGGATAGTTCTCAATTCCTAATAATTCAAAAAATCATTAGGACTGAA

GAAAAATGAATTGCTCAGCATTTTCCTTTTGGTTTGTTTGCAAAATAAT

ATTTTTCTTTCTCTCATTCCATATCCAAATTTCAATAGCTAATCCTCGA

GAAAACTTCCTTAAATGCTTCTCAAAACATATTCCCAACAATGTAGCAA

ATCCAAAACTCGTATACACTCAACACGACCAATTGTATATGTCTATCCT

GAATTCGACAATACAAAATCTTAGATTCATCTCTGATACAACCCCAAAA

CCACTCGTTATTGTCACTCCTTCAAATAACTCCCATATCCAAGCAACTA

TTTTATGCTCTAAGAAAGTTGGCTTGCAGATTCGAACTCGAAGCGGTGG

CCATGATGCTGAGGGTATGTCCTACATATCTCAAGTCCCATTTGTTGTA

GTAGACTTGAGAAACATGCATTCGATCAAAATAGATGTTCATAGCCAAA

CTGCGTGGGTTGAAGCCGGAGCTACCCTTGGAGAAGTTTATTATTGGAT

CAATGAGAAGAATGAGAATCTTAGTTTTCCTGGTGGGTATTGCCCTACT

GTTGGCGTAGGTGGACACTTTAGTGGAGGAGGCTATGGAGCATTGATGC

GAAATTATGGCCTTGCGGCTGATAATATTATTGATGCACACTTAGTCAA

TGTTGATGGAAAAGTTCTAGATCGAAAATCCATGGGAGAAGATCTGTTT

TGGGCTATACGTGGTGGTGGAGGAGAAAACTTTGGAATCATTGCAGCAT

GGAAAATCAAACTGGTTGATGTCCCATCAAAGTCTACTATATTCAGTGT

TAAAAAGAACATGGAGATACATGGGCTTGTCAAGTTATTTAACAAATGG

CAAAATATTGCTTACAAGTATGACAAAGATTTAGTACTCATGACTCACT

TCATAACAAAGAATATTACAGATAATCATGGGAAGAATAAGACTACAGT
```

ACATGGTTACTTCTCTTCAATTTTTCATGGTGGAGTGGATAGTCTAGTC

GACTTGATGAACAAGAGCTTTCCTGAGTTGGGTATTAAAAAAACTGATT

GCAAAGAATTTAGCTGGATTGATACAACCATCTTCTACAGTGGTGTTGT

AAATTTTAACACTGCTAATTTTAAAAAGGAAATTTTGCTTGATAGATCA

GCTGGGAAGAAGACGGCTTTCTCAATTAAGTTAGACTATGTTAAGAAAC

CAATTCCAGAAACTGCAATGGTCAAAATTTTGGAAAAATTATATGAAGA

AGATGTAGGAGCTGGGGTGTTGTACCCTTACGGTGGTATAATGGAGGAG

ATTTCAGAATCAGCAATTCCATTCCCTCATCGAGCTGGAATAATGTATG

AACTTTGGTACACTGCTTCCTGGGAGAAGCAAGAAGATAATGAAAAGCA

TATAAACTGGGTTCGAAGTGTTTATAATTTTACGACTCCTTATGTGTCC

CAAAATCCAAGATTGGCGTATCTCAATTATAGGGACCTTGATTTAGGAA

AAACTAATCATGCGAGTCCTAATAATTACACACAAGCACGTATTTGGGG

TGAAAAGTATTTTGGTAAAAATTTTAACAGGTTAGTTAAGGTGAAAACT

AAAGTTGATCCCAATAATTTTTTTAGAAACGAACAAAGTATCCCACCTC

TTCCACCGCATCATCATTAATTATCTTTAAATAGATATATTTCCCTTAT

CAATTAGTTAATCATTATACCATACATACATTTATTGTATATAGTTTAT

CTACTCATATTATGTATGCTCCCAAGTATGAAAATCTACATTAGAACTG

TGTAGACAATCATA

In some embodiments, a *Cannabis* plant genome includes a CBDA synthase gene sequence. In some embodiments, a *Cannabis* plant genome includes a wild-type CBDA synthase gene sequence. In some embodiments, a *Cannabis* plant genome is homozygous for a wild-type CBDA synthase gene sequence. In some embodiments, a *Cannabis* plant genome is heterozygous for a wild-type CBDA synthase gene sequence. In some embodiments, a *Cannabis* plant genome is homozygous for a variant CBDA synthase gene sequence. In some embodiments, a *Cannabis* plant genome is heterozygous for a variant CBDA synthase gene sequence. In some embodiments, a variant CBDA synthase gene sequence comprises a deletion. In some embodiments, a variant CBDA synthase gene sequence comprises a deletion of a sequence comprising CGTA (SEQ ID NO:3). In some embodiments, a *Cannabis* plant genome includes a CBDA synthase gene sequence that is or comprises a sequence that is 70%, 75%, 80%, 85%, 85%, 87%, 88%, 89%, 90%, 91%, 92%, 93%, 94%, 95%, 96%, 97%, 98%, 99%, or 100% identical to SEQ ID NO: 2, or a portion thereof.

Exemplary *C. sativa* CBDA synthase gene sequence
SEQ ID NO: 2
GATATATATCTCACACGGATGCACCTAACAATGATGCCTAATTTTTGTG

AATTTTTTTTACCACATGACTTAATGATATCAAATTATGAAATATTTAG

TTAATTTATTTGCCCCTGCTCCAATATATAAAGCTATAAATAGGATAGT

TCTTAATCCATAGTAATT

CAAAATTCATTAGAACTAAAGAAAAATGAAGTGCTCAACATTCTCCTTT

TGGTTTGTTTGCAAGATAATATTTTTCTTTTTCTCATTCAATATCCAAA

CTTCCATTGCTAATCCTCGAGAAAACTTCCTTAAATGCTTCTCGCAATA

TATTCCCAATAATGCAACAAATCTAAAACTCGTATACACTCAAAACAAC

CCATTGTATATGTCTGTCCTAAATTCGACAATACACAATCTTAGATTCA

CCTCTGACACAACCCCAAAACCACTTGTTATCGTCACTCCTTCACATGT

CTCTCATATCCAAGGCACTATTCTATGCTCCAAGAAAGTTGGCTTGCAG

ATTCGAACTCGAAGTGGTGGTCATGATTCTGAGGGCATGTCCTACATAT

CTCAAGTCCCATTTGTTATAGTAGACTTGAGAAACATGCGTTCAATCAA

AATAGATGTTCATAGCCAAACTGCATGGGTTGAAGCGGAGCTACCCTT

GGAGAAGTTTATTATTGGGTTAATGAGAAAAATGAGAATCTTAGTTTGG

CGGCTGGGTATTGCCCTACTGTTTGCGCAGGTGGACACTTTGGTGGAGG

AGGCTATGGACCATTGATGAGAAACTATGGCCTCGCGGCTGATAATATC

ATTGATGCACACTTAGTCAACGTTCATGGAAAAGTGCTAGATCGAAAAT

CTATGGGGAAGATCTCTTTTGGGCTTTACGTGGTGGTGGAGCAGAAAG

CTTCGGAATCATTGTAGCATGGAAAATTAGACTGGTTGCTGTCCCAAAG

TCTACTATGTTTAGTGTTAAAAAGATCATGGAGATACATGAGCTTGTCA

AGTTAGTTAACAAATGGCAAAATATTGCTTACAAGTATGACAAAGATTT

ATTACTCATGACTCACTTCATAACTAGGAACATTACAGATAATCAAGGG

AAGAATAAGACAGCAATACACACTTACTTCTCTTCAGTTTTCCTTGGTG

GAGTGGATAGTCTAGTCGACTTGATGAACAAGAGTTTTCCTGAGTTGGG

TATTAAAAAAACGGATTGCAGACAATTGAGCTGGATTGATACTATCATC

TTCTATAGTGGTGTTGTAAATTACGACACTGATAATTTTAACAAGGAAA

TTTTGCTTGATAGATCCGCTGGGCAGAACGGTGCTTTCAAGATTAAGTT

AGACTACGTTAAGAAACCAATTCCAGAATCTGTATTTGTCCAAATTTTG

GAAAAATTATATGAAGAAGATATAGGAGCTGGGATGTATGCGTTGTACC

CTTACGGTGGTATAATGGATGAGATTTCAGAATCAGCAATTCCATTCCC

TCATCGAGCTGGAATCTTGTATGAGTTATGGTACATATGTAGTTGGGAG

AAGCAAGAAGATAACGAAAAGCATCTAAACTGGATTAGAAATATTTATA

ACTTCATGACTCCTTATGTGTCCAAAAATCCAAGATTGGCATATCTCAA

TTATAGAGACCTTGATATAGGAATAAATGATCCCAAGAATCCAAATAAT

TACACACAAGCACGTATTTGGGGTGAGAAGTATTTTGGTAAAAATTTTG

ACAGGCTAGTAAAAGTGAAAACCCTGGTTGATCCCAATAACTTTTTTAG

AAACGAACAAAGCATCCCACCTCTTCCACGGCATCGTCATTAATGATCT

TAAATAGATCTTTTTCTCTTATTAATTAGTCCTTATAATATACATATAT

TGATTATATATATAAAAATAGTTTGTCCGGGTGTACTGTGTATGCGATA

TATATCTCACAC

In some embodiments, a *Cannabis* plant genome includes an olivetol synthase gene sequence. In some embodiments, a *Cannabis* plant genome includes a wild-type olivetol synthase gene sequence. In some embodiments, a *Cannabis* plant genome is homozygous for a wild-type olivetol synthase gene sequence. In some embodiments, a *Cannabis* plant genome is heterozygous for a wild-type olivetol synthase gene sequence. In some embodiments, a *Cannabis* plant genome is homozygous for a variant olivetol synthase gene sequence. In some embodiments, a *Cannabis* plant genome is heterozygous for a variant olivetol synthase gene sequence. In some embodiments, a *Cannabis* plant genome includes an olivetol synthase gene sequence that is or comprises a sequence that is 70%, 75%, 80%, 85%, 85%, 87%, 88%, 89%, 90%, 91%, 92%, 93%, 94%, 95%, 96%, 97%, 98%, 99%, or 100% identical to SEQ ID NO: 4, or a portion thereof.

```
Exemplary C. sativa olivetol synthase gene
sequence
                                        SEQ ID NO: 4
ATGAATCATCTTCGTGCTGAGGGTCCGGCCTCCGTTCTCGCCATTGGCA

CCGCCAATCCGGAGAACATTTTATTACAAGATGAGTTTCCTGACTACTA

TTTTCGCGTCACCAAAAGTGAACACATGACTCAACTCAAAGAAAAGTTT

CGAAAAATATGTGACAAAAGTATGATAAGGAAACGTAACTGTTTCTTAA

ATGAAGAACACCTAAAGCAAAACCCAAGATTGGTGGAGCACGAGATGCA

AACTCTGGATGCACGTCAAGACATGTTGGTAGTTGAGGTTCCAAAACTT

GGGAAGGATGCTTGTGCAAAGGCCATCAAAGAATGGGGTCAACCCAAGT

CTAAAATCACTCATTTAATCTTCACTAGCGCATCAACCACTGACATGCC

CGGTGCAGACTACCATTGCGCTAAGCTTCTCGGACTGAGTCCCTCAGTG

AAGCGTGTGATGATGTATCAACTAGGCTGTTATGGTGGTGGAACCGTTC

TACGCATTGCCAAGGACATAGCAGAGAATAACAAAGGCGCACGAGTTCT

CGCCGTGTGTTGTGACATAATGGCTTGCTTGTTTCGTGGGCCTTCAGAG

TCTGACCTCGAATTACTAGTGGGACAAGCTATCTTTGGTGATGGGCTG

CTGCGGTGATTGTTGGAGCTGAACCCGATGAGTCAGTTGGGGAAAGGCC

GATATTTGAGTTGGTGTCAACTGGGCAAACAATCTTACCAAACTCGGAA

GGAACTATTGGGGGACATATAAGGGAAGCAGGACTGATATTTGATTTAC

ATAAGGATGTGCCTATGTTGATCTCTAATAATATTGAGAAATGTTTGAT

TGAGGCATTTACTCCTATTGGGATTAGTGATTGGAACTCCATATTTTGG

ATTACACACCCAGGTGGGAAAGCTATTTTGGACAAAGTGGAGGAGAAGT

TGCATCTAAAGAGTGATAAGTTTGTGGATTCACGTCATGTGCTGAGTGA

GCATGGGAATATGTCTAGCTCAACTGTCTTGTTTGTTATGGATGAGTTG

AGGAAGAGGTCGTTGGAGGAAGGGAAGTCTACCACTGGAGATGGATTTG

AGTGGGGTGTTCTTTTTGGGTTTGGACCAGGTTTGACTGTCGAAAGAGT

GGTCGTGCGTAGTGTTCCCATCAAATATTAA
```

In some embodiments, a *Cannabis* plant genome includes a divarinic acid synthase gene sequence. In some embodiments, a *Cannabis* plant genome includes a wild-type divarinic acid synthase gene sequence. In some embodiments, a *Cannabis* plant genome is homozygous for a wild-type divarinic acid synthase gene sequence. In some embodiments, a *Cannabis* plant genome is heterozygous for a wild-type divarinic acid synthase gene sequence. In some embodiments, a *Cannabis* plant genome is homozygous for a variant divarinic acid synthase gene sequence. In some embodiments, a *Cannabis* plant genome is heterozygous for a variant divarinic acid synthase gene sequence.

In some embodiments, a *Cannabis* plant genome includes a limonene synthase gene sequence. In some embodiments, a *Cannabis* plant genome includes a wild-type limonene synthase gene sequence. In some embodiments, a *Cannabis* plant genome is homozygous for a wild-type limonene synthase gene sequence. In some embodiments, a *Cannabis* plant genome is heterozygous for a wild-type limonene synthase gene sequence. In some embodiments, a *Cannabis* plant genome is homozygous for a variant limonene synthase gene sequence. In some embodiments, a *Cannabis* plant genome is heterozygous for a variant limonene synthase gene sequence. In some embodiments, a *Cannabis* plant genome includes a limonene synthase gene sequence that is or comprises a sequence that is 70%, 75%, 80%, 85%, 85%, 87%, 88%, 89%, 90%, 91%, 92%, 93%, 94%, 95%, 96%, 97%, 98%, 99%, or 100% identical to SEQ ID NO: 5, or a portion thereof.

```
Exemplary C. sativa limonene synthase gene
sequence
                                        SEQ ID NO: 5
ATGCAGTGCATAGCTTTTCACCAATTTGCTTCATCATCATCCCTCCCTA

TTTGGAGTAGTATTGATAATCGTTTTACACCAAAAACTTCTATTACTTC

TATTTCAAAACCAAAACCAAAACTAAAATCAAAATCAAACTTGAAATCG

AGATCGAGATCAAGTACTTGCTACTCCATACAATGTACTGTGGTCGATA

ACCCTAGTTCTACGATTACTAATAATAGTGATCGAAGATCAGCCAACTA

TGGACCTCCCATTTGGTCTTTTGATTTTGTTCAATCTCTTCCAATCCAA

TATAAGGGTGAATCTTATACAAGTCGATTAAATAAGTTGGAGAAAGATG

TGAAAAGGATGCTAATTGGAGTGGAAAACTCTTTAGCCCAACTTGAACT

AATTGATACAATACAAAGACTTGGAATATCTTATCGTTTTGAAAATGAA

ATCATTTCTATTTTGAAAGAAAAATTCACCAATAATAATGACAACCCTA

ATCCTAATTATGATTTATATGCTACTGCTCTCCAATTTAGGCTTCTACG

CCAATATGGATTTGAAGTACCTCAAGAAATTTTCAATAATTTTAAAAAT

CACAAGACAGGAGAGTTCAAGGCAAATATAAGTAATGATATTATGGGAG

CATTGGGCTTATATGAAGCTTCATTCCATGGGAAAAAGGGTGAAAGTAT

TTTGGAAGAAGCAAGAATTTTCACAACAAAATGTCTCAAAAAATACAAA

TTAATGTCAAGTAGTAATAATAATAATATGACATTAATATCATTATTAG

TGAATCATGCTTTGGAGATGCCACTTCAATGGAGAATCACAAGATCAGA

AGCTAAATGGTTTATTGAAGAAATATATGAAAGAAAACAAGACATGAAT

CCAACTTTACTTGAGTTTGCCAAATTGGATTTCAATATGCTGCAATCAA

CATATCAAGAGGAGCTCAAAGTACTCTCTAGGTGGTGGAAGGATTCTAA

ACTTGGAGAGAAATTGCCTTTCGTTAGAGATAGATTGGTGGAGTGTTTC

TTATGGCAAGTTGGAGTAAGATTTGAGCCACAATTCAGTTACTTTAGAA

TAATGGATACAAAACTCTATGTTCTATTAACAATAATTGATGATATGCA

TGACATTTATGGAACATTGGAGGAACTACAACTTTTCACTAATGCTCTT

CAAAGATGGGATTTGAAAGAATTAGATAAATTACCAGATTATATGAAGA

CAGCTTTCTACTTTACATACAATTTCACAAATGAATTGGCATTTGATGT

ATTACAAGAACATGGTTTTGTTCACATTGAATACTTCAAGAAACTGATG

GTAGAGTTGTGTAAACATCATTTGCAAGAGGCAAAATGGTTTTATAGTG

GATACAAACCAACATTGCAAGAATATGTTGAGAATGGATGGTTGTCTGT

GGGAGGACAAGTTATTCTTATGCATGCATATTTCGCTTTTACAAATCCT
```

```
-continued
GTTACCAAAGAGGCATTGGAATGTCTAAAAGACGGTCATCCTAACATAG

TTCGCCATGCATCGATAATATTACGACTTGCAGATGATCTAGGAACATT

GTCGGATGAACTGAAAAGAGGCGATGTTCCTAAATCAATTCAATGTTAT

ATGCACGATACTGGTGCTTCTGAAGATGAAGCTCGTGAGCACATAAAAT

ATTTAATAAGTGAATCATGGAAGGAGATGAATAATGAAGATGGAAATAT

TAACTCTTTTTTCTCAAATGAATTTGTTCAAGTTTGCCAAAATCTTGGT

AGAGCGTCACAATTCATATACCAGTATGGCGATGGACATGCTTCTCAGA

ATAATCTATCGAAAGAGCGCGTTTTAGGGTTGATTATTACTCCTATCCC

CATGTAA
```

Classification of *Cannabis*

Provided herein is a recognition that certain genotypes are associated with altered cannabinoid synthesis or an altered cannabinoid profile. Genetic information can positively benefit consumers, growers, and regulators of *Cannabis*. There are at least several hundred compounds found in *Cannabis* and currently only a fraction of these compounds are analyzed. As used herein, chemotype of a *Cannabis* plant refers to an abundance and/or deficiency of one or more compounds found in a *Cannabis* plant (e.g., cannabinoids, flavonoids and/or terpenes). In some embodiments, a chemotype is an abundance of one or more cannabinoids, flavonoids and/or terpenes. In some embodiments, a chemotype is a relative amount of two or more cannabinoids, flavonoids and/or terpenes.

Chemotype determination has been limited as quantitative analytical techniques and standards do not currently exist for all *Cannabis* compounds. As a result, previously described chemotypes fail to capture the chemical and potential medicinal complexity in a *Cannabis* plant. The present disclosure encompasses a recognition that genetic analysis, for example, of one, two, three, four, five or more synthetic enzymes, can serve as a proxy for unmeasured chemical complexity.

The present disclosure encompasses the recognition that genetic analysis can be used to assess the potential of a *Cannabis* plant to produce certain compounds, such as cannabinoids, flavonoids and/or terpenes. While a *Cannabis* plant can be raised under conditions that result in varied expression and/or concentrations of certain compounds, the relative ratios of key chemotypic gene sequences, such as, for example, THCA synthase and CBDA synthase, are usually genetically determined. For example, there are currently no known agricultural methods to make a CBD-dominant *Cannabis* strain become a THC-dominant *Cannabis* strain via environmental conditions. These critical chemotypes are governed by genetic alterations in their respective enzymatic synthases (e.g., CDBA synthase and THCA synthase).

In some embodiments, methods of the present disclosure include genetic analysis of one, two, three, four, five or more enzymes involved in the production of cannabinoids, flavonoids and/or terpenes. In some embodiments, methods of the present disclosure include amplification of a genomic region that encodes an enzyme involved in the production of a cannabinoid, flavonoid and/or terpene. In some embodiments, methods of the present disclosure include amplification of a plurality of genomic regions that encode enzymes involved in the production of a cannabinoid, flavonoid and/or terpene. In some embodiments, methods include amplification of a portion of a gene sequence that encodes an enzyme involved in the production of a cannabinoid, flavonoid and/or terpene.

Genetic prediction of cannabinoid production has been an active area of study. See, for example, Weiblen et al., (2015), *The New Phytologist*, PMID: 26189495; Marks et al., (2009) *Journal of Experimental Botany*, 60(13):3715-26, PMID: 19581347; Onofri et al., (2015) *Phytochemistry*, 116:57-68, PMID: 25865737; de Meijer et al. (2003) *Genetics*, 163(1): 335-46, PMID: 12586720; and Kojoma et al. (2006), *Forensic Sci. Int.*, 159(2-3):132-40, PMID: 16143478, each of which is incorporated herein by reference. However, there are significant caveats and shortcomings with prior methods of genetic prediction of cannabinoid production. For example, while alleles of Bt (functional THCA synthase) and Bd (functional CBDA synthase) have been proposed as a model for generating Type I, II, III, and IV plants, the exact DNA sequences that govern these alleles remain unknown. As described in the examples herein, single molecule sequencing was performed to identify mutations in gene sequences in cannabinoid synthesis pathway enzyme(s) (e.g., THCA synthase and CBDA synthase). This sequencing revealed a more refined structure of inheritance and numerous additional subtypes that can be identified by genotyping to predict chemical inheritance. See, FIG. 2.

Kitamura describes amplification of a small region of THCA synthase to resolve hemp from drug-type (i.e., THC expressing) strains. Kitamura et al., (2017) *Journal of natural medicines*, 71 (1):86-95, PMID: 27535292 and Kitamura et al., (2016) *Biological & pharmaceutical bulletin*, 39 (7):1144-9, PMID: 27118244, each of which is incorporated herein by reference. However, the present disclosure recognizes that these studies only tested 3 cultivars and also failed to consider CBDA status. The present disclosure encompasses a recognition that an understanding CBDA status is critical for determining allelic balance of CBDA and THCA synthases, which may be important for *Cannabis* breeding efforts.

*Cannabis* genomes are about 10 fold more variable than human genomes. Moreover, a given *Cannabis* strain is often capable of crossing with highly divergent *Cannabis* strains (e.g., *Cannabis* strains of a different chemotype, genotype, etc.). As a result, even sibling strains cannot be not be assumed to have the same chemotype. The present disclosure provides methods and kits suitable for genetic characterization of individual *Cannabis* plants.

In some embodiments, a method includes detection of one or a plurality of sequences that include a gene sequence or portion thereof in a sample that comprises nucleic acid from a *Cannabis* plant. In some embodiments, a gene sequence encodes an enzyme involved in the synthesis of one or more cannabinoids.

In some embodiments, a method of the present disclosure includes detecting the presence of a tetrahydrocannabinolic acid (THCA) synthase gene sequence or a portion thereof. The present disclosure encompasses the recognition that THCA synthase is under selective breeding pressure and has approximately a 4 fold higher polymorphism rate than a *Cannabis* genome in general. Moreover, a THCA synthase gene sequence can include a SNP approximately every 25 nucleotides, which complicates design of primers that anneal within the open reading frame of THCA synthase. In some embodiments, a THCA synthase gene sequence encodes a wildtype THCA synthase enzyme (i.e., functional). In some embodiments, a THCA synthase gene sequence includes a THCA synthase gene sequence promoter sequence. In some embodiments, a THCA synthase gene sequence includes a THCA synthase gene sequence 5' UTR sequence.

In some embodiments, a method of the present disclosure includes amplifying a THCA synthase gene sequence or portion thereof from a sample that comprises nucleic acid from a *Cannabis* plant. In some embodiments, amplification of a THCA synthase gene sequence includes contacting nucleic acid from a *Cannabis* plant with a forward THCA synthase primer that is complementary to a sequence that is 200-1000 nucleotides upstream of a THCA open reading frame. In some embodiments, a forward THCA synthase primer is complementary to a sequence that is 200 to 800 nucleotides, 200 to 600 nucleotides, 200 to 400 nucleotides upstream of a THCA open reading frame. In some certain embodiments, a forward THCA synthase primer is complementary to a sequence that is at least 70%, 75%, 80%, 85%, 85%, 87%, 88%, 89%, 90%, 91%, 92%, 93%, 94%, 95%, 96%, 97%, 98%, 99%, or 100% identical to a portion of SEQ ID NO: 6. In some certain embodiments, a forward THCA synthase primer is at 20 to 60 nucleotides long.

```
Exemplary C. sativa sequence upstream of THCA
synthase open reading frame
                                          SEQ ID NO: 6
CATAGCGACTATCGTGATGGGAACCATAATAAACTATAAAAGTCATTAT

GTGTACTTGCTACCATAGGCACCTATATCCCACAAACTAGCTACCATAG

CCAATTTCTTTTTTGTTTCCAATATCCAATTTTTATTGATGCCAAACTA

TTCAATGTACAATGTACATTTATTTTCAATAAGGGCTTCACCTAACAAA

GGTGCCTAATTTTAGTTGATTTATTTTTTATCACATGTGACTATTTAAT

GACTATCAAATTATAAAATATTTAAGTCAATTTATTTGCCCCAACTCCA

ATATATAATATTATAAATAGGATAGTTCTCAATTCCTAATAATTCAAAA

AATCATTA
```

In some embodiments, amplification of a THCA synthase gene sequence includes contacting nucleic acid from a *Cannabis* plant with a reverse THCA synthase primer that is complementary to a sequence that is 200-1000 nucleotides downstream of a THCA open reading frame. In some embodiments, a reverse THCA synthase primer is complementary to a sequence that is 200 to 800 nucleotides, 200 to 600 nucleotides, 200 to 400 nucleotides downstream of a THCA open reading frame. In some certain embodiments, a reverse THCA synthase primer is complementary to a sequence that is at least 70%, 75%, 80%, 85%, 85%, 87%, 88%, 89%, 90%, 91%, 92%, 93%, 94%, 95%, 96%, 97%, 98%, 99%, or 100% identical to a portion of SEQ ID NO: 7. In some certain embodiments, a reverse THCA synthase primer is about 20 to 60 nucleotides long.

```
Exemplary C. sativa sequence downstream of THCA
synthase open reading frame
                                          SEQ ID NO: 7
TTATCAATTAGTTAATCATTATACCATACATACATTTATTGTATATAGT
TTATCTACTCATATTATGTATGCTCCCAAGTATGAAAATCTACATTAGA
ACTGTGTAGACAATCATACATAGCGACTATCGTG
```

In some embodiments, amplification of a THCA synthase gene sequence includes contacting nucleic acid from a *Cannabis* plant with two or more primers that are at least 70%, 75%, 80%, 85%, 85%, 87%, 88%, 89%, 90%, 91%, 92%, 93%, 94%, 95%, 96%, 97%, 98%, 99%, or 100% identical to any of SEQ ID NOs: 8-12.

In some embodiments, a method of the present disclosure includes detecting the presence of a variant THCA synthase gene sequence in a sample that comprises nucleic acid from the *Cannabis* plant. In some embodiments, a method of the present disclosure includes amplifying a variant THCA synthase gene sequence or portion thereof from a sample that comprises nucleic acid from a *Cannabis* plant.

In some embodiments, a method of the present disclosure includes detecting the presence of a mutated THCA synthase gene sequence in a sample that comprises nucleic acid from the *Cannabis* plant. In some embodiments, a mutated THCA synthase gene sequence includes at least one mutation that alters the activity of a THCA synthase encoded by the mutated THCA synthase gene sequence relative to a THCA synthase encoded by a wild-type THCA synthase gene sequence.

Figure 3:
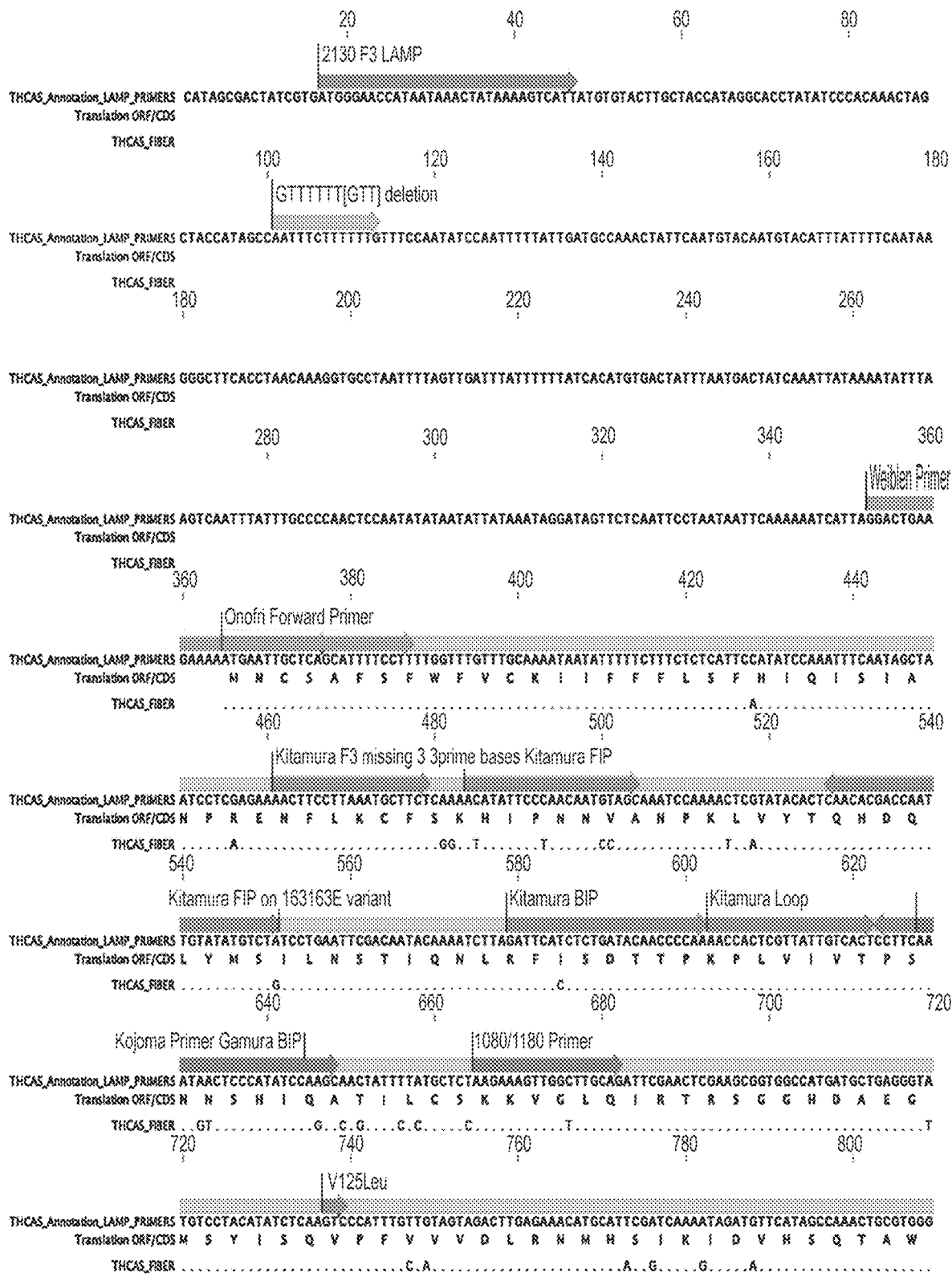
FIG. 3: depicts an alignment of various primers sequences with the sequence of a *Cannabis* THCA synthase gene sequence (SEQ ID NO: 20). Exemplary mutations in a THCA synthase gene sequence are provided along THCAS-FIBER dotted underneath the ORF/CDS sequence.
Figure 3:
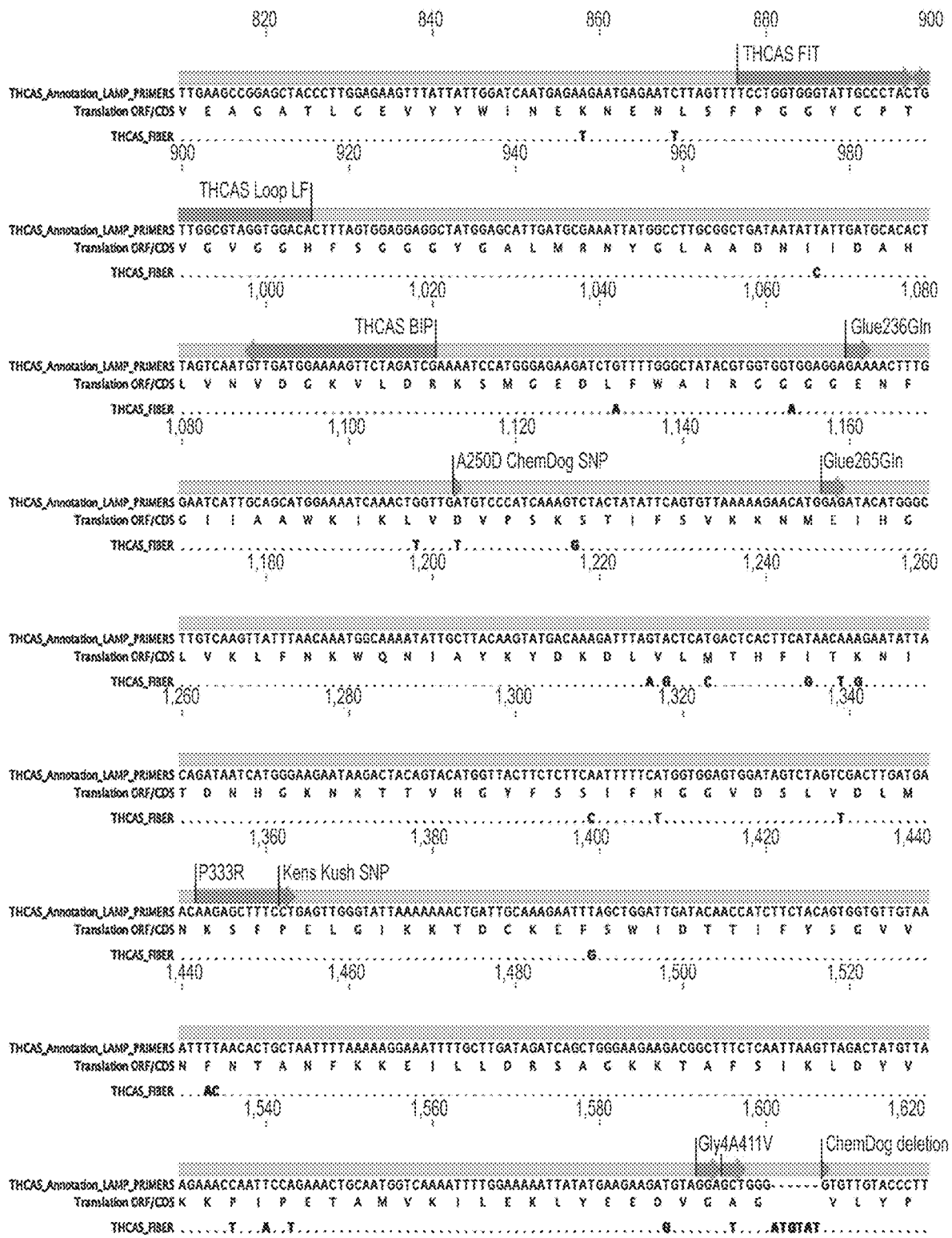
Figure 3:
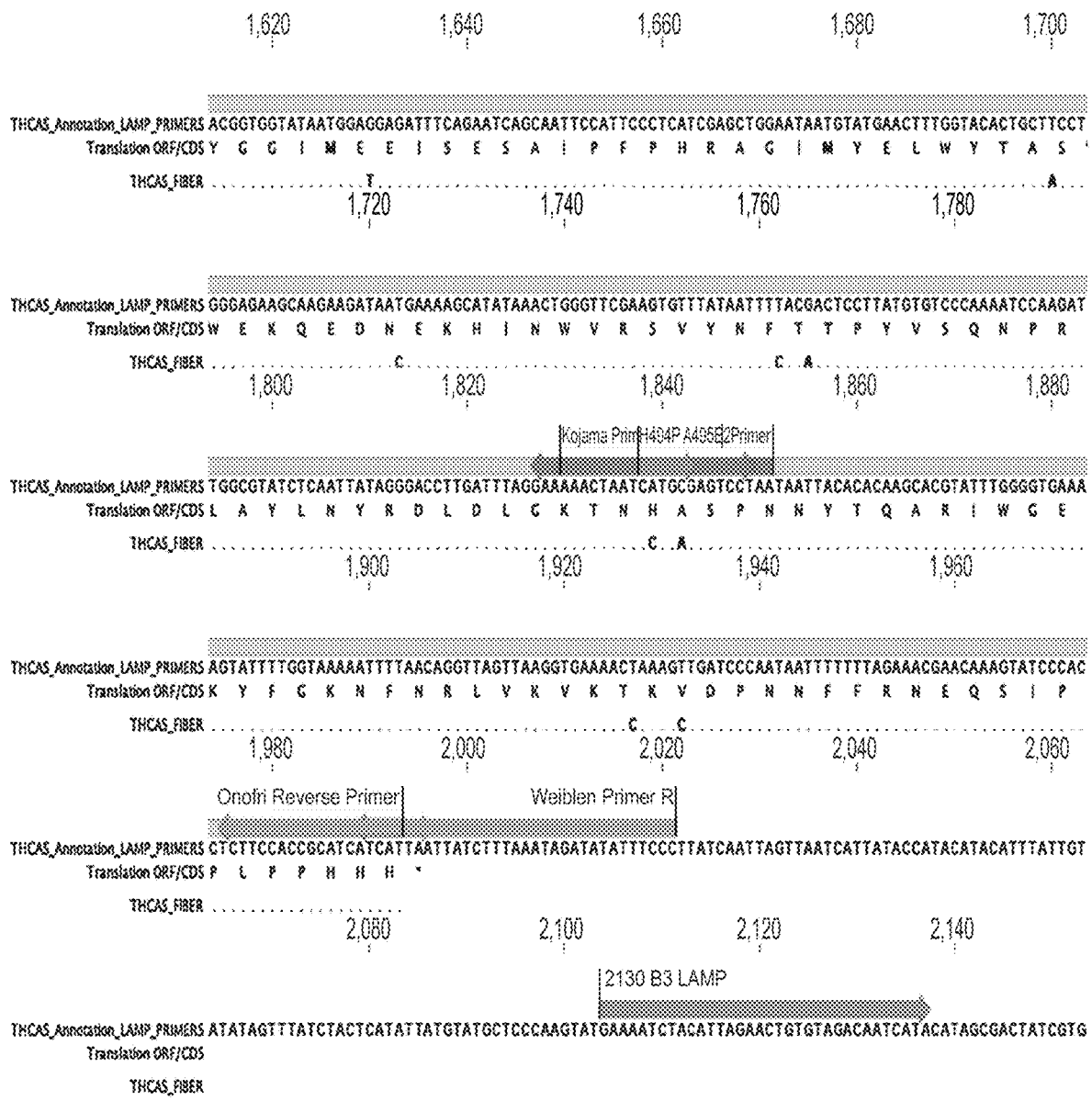

In some embodiments, a method of the present disclosure includes detecting the presence of a polymorphism within a THCA synthase gene sequence in a sample that comprises nucleic acid from the *Cannabis* plant. In some embodiments, a polymorphism within a THCA synthase gene sequence is or comprises one or more variants as described in FIG. 3 and/or FIG. 10. FIG. 10 prevents a chart describing certain Single Nucleotide Polymorphism (SNP) variants of THCA synthase in different *Cannabis* plant strains (indicated by accession code). SNPs that result in an amino acid change are indicated in bold, and the type of change is with the corresponding position in the amino acid sequence is indicated in the bottom row. In the last column is provided the proportion of THC(V)A product of the total cannabinoid fraction that is accumulated in each *Cannabis* plant variant. In some embodiments, a THCA synthase gene sequence is or comprises a I63L variant, a V125L variant, a E236Q variant, a A250D variant, a E265G variant, and/or a G410E variant. In some certain embodiments, a THCA synthase gene sequence is or comprises a A411V variant.

In some embodiments, a method of the present disclosure includes detecting the presence of a wild-type cannabidiolic acid ($CBDA^{WT}$) synthase gene sequence in a sample that comprises nucleic acid from the *Cannabis* plant. In some embodiments, a method of the present disclosure includes amplifying a $CBDA^{WT}$ synthase gene sequence or portion thereof from a sample that comprises nucleic acid from a *Cannabis* plant.

In some embodiments, a method of the present disclosure includes detecting the presence of a mutated cannabidiolic acid ($CBDA^{mut}$) synthase gene sequence in a sample that comprises nucleic acid from the *Cannabis* plant, wherein the mutated CBDA synthase gene sequence comprises a deletion mutation. In some embodiments, a $CBDA^{del}$ sequence includes or comprises a deletion of CGTA (SEQ ID NO:3). In some embodiments, a method of the present disclosure includes amplifying a $CBDA^{mut}$ synthase gene sequence or portion thereof from a sample that comprises nucleic acid from a *Cannabis* plant. In some embodiments, a method of the present disclosure includes amplifying a $CBDA^{del}$ synthase gene sequence or portion thereof from a sample that comprises nucleic acid from a *Cannabis* plant.

In some embodiments, a method of the present disclosure includes detecting a combination of two or more genomic sequences selected from: a THCA synthase gene sequence, a variant or mutant THCA synthase gene sequence, a $CBDA^{WT}$ synthase, and $CBDA^{mut}$ synthase gene sequence. In some embodiments, a method of the present disclosure includes amplifying two or more genomic sequences selected from: a THCA synthase gene sequence, a variant or mutant THCA synthase gene sequence, a $CBDA^{WT}$ synthase, and CBDA$^{mut}$ synthase gene sequence, from a sample that comprises nucleic acid from a *Cannabis* plant.

In some embodiments, a method of the present disclosure includes detecting the presence of an olivetol synthase gene sequence in a sample that comprises nucleic acid from a *Cannabis* plant. In some embodiments, a method of the present disclosure includes amplifying an olivetol synthase gene sequence or portion thereof from a sample that comprises nucleic acid from a *Cannabis* plant. In some embodiments, a method of the present disclosure includes detecting the presence of a variant olivetol synthase gene sequence in a sample that comprises nucleic acid from a *Cannabis* plant. In some embodiments, a method of the present disclosure includes amplifying a variant olivetol synthase gene sequence or portion thereof from a sample that comprises nucleic acid from a *Cannabis* plant.

In some embodiments, a method of the present disclosure includes detecting the presence of a divarinic acid synthase gene sequence in a sample that comprises nucleic acid from a *Cannabis* plant. In some embodiments, a method of the present disclosure includes amplifying a divarinic acid synthase gene sequence or portion thereof from a sample that comprises nucleic acid from a *Cannabis* plant. In some embodiments, a method of the present disclosure includes detecting the presence of a variant divarinic acid synthase gene sequence in a sample that comprises nucleic acid from a *Cannabis* plant. In some embodiments, a method of the present disclosure includes amplifying a variant divarinic acid synthase gene sequence or portion thereof from a sample that comprises nucleic acid from a *Cannabis* plant.

In some embodiments, a method of the present disclosure includes detecting the presence of a limonene synthase gene sequence in a sample that comprises nucleic acid from a *Cannabis* plant. In some embodiments, a method of the present disclosure includes amplifying a limonene synthase gene sequence or portion thereof from a sample that comprises nucleic acid from a *Cannabis* plant. In some embodiments, a method of the present disclosure includes detecting the presence of a variant limonene synthase gene sequence in a sample that comprises nucleic acid from a *Cannabis* plant. In some embodiments, a method of the present disclosure includes amplifying a variant limonene synthase gene sequence or portion thereof from a sample that comprises nucleic acid from a *Cannabis* plant.

In some embodiments, a method of the present disclosure includes detecting a combination of two, three, four, five, six, seven, eight, or more genomic sequences selected from: a THCA synthase gene sequence, a variant or mutant THCA synthase gene sequence, a CBDA$^{WT}$ synthase, and CBDA$^{mut}$ synthase gene sequence. In some embodiments, a method of the present disclosure includes amplifying two or more genomic sequences selected from: a THCA synthase gene sequence, a variant or mutant THCA synthase gene sequence, a CBDA$^{WT}$ synthase, a CBDA$^{mut}$ synthase gene sequence, a olivetol synthase gene sequence, a variant olivetol synthase gene sequence, a divarinic acid synthase gene sequence, a variant divarinic acid synthase gene sequence, a limonene synthase gene sequence, and a variant limonene synthase gene sequence from a sample that comprises nucleic acid from the *Cannabis* plant.

Methods for Genotyping *Cannabis*

In vitro nucleic acid amplification technique can be used for genotyping *Cannabis* plants. In vitro nucleic acid amplification techniques can be grouped according to the temperature requirements of the procedure. For example, polymerase chain reaction (PCR) is the most popular method used as a technique of amplifying nucleic acid in vitro. PCR has high sensitivity based on the effect of exponential amplification. Further, since a PCR amplification product can be recovered as DNA, this method is applied widely for genetic engineering techniques such as gene sequence cloning and structural determination. In PCR, however, temperature cycling or a special temperature controller is necessary for practice; the exponential progress of the amplification reaction causes a problem in quantification. Other PCR-based amplification techniques include, for example, transcription-based amplification (D. Y. Kwoh, et at. 1989. Proc. Natl. Acad Sci. USA 86, 1173-1177, which is incorporated herein by reference), ligase chain reaction (LCR; D. Y. Wu, et al. 1989. Genomics 4, 560-569; K. Barringer, et al. 1990. Gene 89, 117-122; F. Barany. 1991. Proc. Natl. Acad. Sci. USA 88, 189-193, each of which are incorporated herein by reference), and restriction amplification (U.S. Pat. No. 5,102,784, which is incorporated herein by reference).

More recently, a number of isothermal nucleic acid amplification techniques have been developed. That is, these techniques do not rely on thermocycling to drive nucleic acid amplification. Isothermal amplification techniques typically utilize DNA polymerases with strand-displacement activity, thus eliminating the high temperature melt cycle that is required for PCR. This allows isothermal techniques to be faster and more energy efficient than PCR, and also allows for more simple and thus lower cost instrumentation since rapid temperature cycling is not required. For example, methods such as Strand Displacement Amplification (SDA; Walker, et at., (1992) *Proc. Natl. Acad. Sci. USA* 89: 392-396; Walker, et al., (1992) *Nuc. Acids. Res.* 20:1691-1696; U.S. Pat. No. 5,648,211 and EP 0 497 272, each of which is incorporated herein by reference); self-sustained sequence replication (3SR; J. C. Guatelli, et al., (1990) *Proc. Natl. Acad. Sci. USA*, 87: 1874-1878, which is incorporated herein by reference); and Qβ replicase system (Lizardi, et al., (1988) *BioTechnology,* 6: 1197-1202, which is incorporated herein by reference) are isothermal reactions. See also, Nucleic Acid Isothermal Amplification Technologies—A Review. Nucleosides, Nucleotides and Nucleic Acids (2008) v27(3):224-243, which is incorporated herein by reference.

In some embodiments, an in vitro nucleic acid amplification assay for use in the methods of the present disclosure is an isothermal amplification method. Isothermal amplification methods include, for example, transcription mediated amplification (TMA) or self-sustained sequence replication (3SR), nucleic acid sequence-based amplification (NASBA), signal mediated amplification of RNA technology (SMART), strand displacement amplification (SDA), rolling circle amplification (RCA), loop-mediated isothermal amplification of DNA (LAMP), isothermal multiple displacement amplification (IMDA), helicase-dependent amplification (HDA), single primer isothermal amplification (SPIA), and circular helicase-dependent amplification (cHDA))

LAMP Assay

It is envisioned that LAMP amplification assays as described herein will provides a rapid and scalable means to resolve chemotypes of *Cannabis* plants. In some embodiments, an in vitro nucleic acid amplification assay for use in the methods of the present disclosure is Loop-Mediated Isothermal Amplification (LAMP). Typically, LAMP reactions use a strand-displacing DNA polymerase with four to six primers, which can result in exponential amplification of a target sequence.

In LAMP, a target sequence is amplified at a constant temperature. In some embodiments, a LAMP reaction temperature is between 37° C. and 75° C. In some embodiments, a LAMP reaction temperature is between 50° C. and 70° C. In some embodiments, a LAMP reaction temperature is between 55° C. and 65° C. In some embodiments, a LAMP reaction temperature is between 60° C. and 65° C. In some embodiments, a LAMP reaction uses two or three primer sets, and a polymerase with high strand displacement activity in addition to a replication activity. (See Nagamine et al., (2002) Mol. Cell. Probes 16 (3): 223-9; and U.S. Pat. No. 6,410,278, each of which is incorporated herein by reference).

LAMP was originally invented and formulated as an isothermal amplification with a requirement for four primers: two loop-generating primers (FIP and BIP comprising F1, F2 and B1, B2 priming sites, correspondingly) and two "Displacement primers" (F3 and B3). In order to increase the speed of LAMP-based assays additional "Loop primers" were added in conjunction with the other primers used in LAMP, which resulted in significantly faster assays.

In some embodiments, LAMP amplification of a THCA synthase gene sequence includes contacting nucleic acid from a *Cannabis* plant with four or more primers that are at least 70%, 75%, 80%, 85%, 87%, 88%, 89%, 90%, 91%, 92%, 93%, 94%, 95%, 96%, 97%, 98%, 99%, or 100% identical to any of SEQ ID NOs: 8-12.

In some embodiments, LAMP amplification of a CBDA synthase gene sequence includes contacting nucleic acid from a *Cannabis* plant with four, five, or six, or more primers that are at least 70%, 75%, 80%, 85%, 85%, 87%, 88%, 89%, 90%, 91%, 92%, 93%, 94%, 95%, 96%, 97%, 98%, 99%, or 100% identical to any of SEQ ID NOs: 13-18 and 27.

In some embodiments, LAMP amplification of a $CBDA^{mut}$ ($CBDA^{del}$) synthase gene sequence includes contacting nucleic acid from a *Cannabis* plant with four, five, or six, or more primers that are at least 70%, 75%, 80%, 85%, 85%, 87%, 88%, 89%, 90%, 91%, 92%, 93%, 94%, 95%, 96%, 97%, 98%, 99%, or 100% identical to any of SEQ ID NOs: 13, 15-19, and 27.

In some embodiments, a LAMP amplification assay as described herein is a colorimetric LAMP assay.

Due to the specific nature of the action of these primers, the amount of DNA produced in LAMP is considerably higher than PCR based amplification. The reaction can be followed in real-time either by measuring the turbidity or by fluorescence using intercalating dyes. Dye molecules intercalate or directly label the DNA, and in turn can be correlated to the number of copies initially present. Hence, LAMP can also be quantitative. Thus, LAMP provides major advantages due to its simplicity, ruggedness, and low cost, and has the potential to be used as a simple screening assay in the field or at the point of care by clinicians.

Primer design for LAMP assays generally involves selection of eight separate regions of a target nucleic acid sequence (the FIP and BIP primers encompass two primer binding sites each), with BIP/FIP and Loop primers having significant restrictions on their positioning respective to each other. "Loop primers" are positioned between B2 and B1 sites and F2 and F1 sites, respectively, and must be orientated in a particular direction. Further, significant care must be taken in primer design to avoid primer-dimers between the six primers (which can be especially difficult as the FIP and BIP primers are generally greater than 40 nucleotides long). As a consequence, LAMP primer design is extremely challenging, especially when targeting highly polymorphic markers and sequences containing complex secondary structure. At least in part because primer design for LAMP is subject to numerous constraints, software is generally used to assist with LAMP primer design.

LAMP has been observed to be less sensitive than PCR to inhibitors in complex samples such as blood, likely due to use of a different DNA polymerase (typically Bst DNA polymerase rather than Taq polymerase as in PCR). LAMP is useful primarily as a diagnostic or detection technique, but is generally not useful for some molecular biology applications enabled by PCR, such as, for example, cloning.

Also, multiplexing approaches for LAMP are relatively undeveloped. The larger number of primers per target in LAMP increases the likelihood of primer-primer interactions for multiplexed target sets. The product of LAMP is a series of concatemers of the target region, giving rise to a characteristic "ladder" or banding pattern on a gel, rather than a single band as with PCR. Although this is not a problem when detecting single targets with LAMP, "traditional" (endpoint) multiplex PCR applications wherein identity of a target is confirmed by size of a band on a gel are not feasible with LAMP. Multiplexing in LAMP has been achieved by choosing a target region with a restriction site, and digesting prior to running on a gel, such that each product gives rise to a distinct size of fragment, although this approach adds complexity to the experimental design and protocol. The use of a strand-displacing DNA polymerase in LAMP also precludes the use of hydrolysis probes, e.g. TaqMan probes, which rely upon the 5'-3' exonuclease activity of Taq polymerase.

In some embodiments, a modified LAMP technique called LAMP-STEM is used in a method of the present disclosure. LAMP-STEM system utilizes "Stem primers," which are directed to the stem portion of the LAMP amplicon (or "dumbbell"). Stem primers can be used as an alternative to LAMP "Loop primers." When used in addition to loop-generating and displacement primers, Stem primers offer similar benefits in speed and sensitivity to the Loop primers. (See Gandelman et al., Loop-Mediated Amplification Accelerated by Stem Primers. Int. J. Mol. Sci. 2011, v12:9108-9124, and US 2012/0157326, each of which is incorporated herein by reference). This beneficial effect of Stem primers is surprising as they do not bind to the single-stranded DNA loops, which define the very nature of the LAMP technology. Stem primers can be employed in either orientation, do not require either the B2/B1 or F2/F1 sites to be a specific distance apart, can be multiplexed, and allow the F1 and B1 sites to be positioned further from each other than in LAMP.

Stem primers significantly accelerate LAMP comprised of loop-generating and displacement primers only. They can be used on their own or synergistically with other Stem primers or even Loop primers. Addition of Stem primers into LAMP has a positive effect on both speed and sensitivity. In some cases they improve reproducibility at low copy number. The action of Stem primers can be rationalized via the proposed mechanism of LAMP. They anneal to transiently single-stranded regions of the amplicon and recopy the entire binding sites for the BIP/FIP primers. An additional unique feature is the extra strong intra-molecular self-priming when Stem primers delimit amplicon.

In general, positioning of Stem primers is less constrained than that of Loop primers. A rather challenging primer design involving selection of at least eight binding sites is thus simplified. Furthermore, Stem primers impose fewer limitations on the primer design in terms of stem length, orientation and distances between B1-B2 and F1-F2 sites. In contradiction to the postulated LAMP mechanism that relies on the involvement of displacement primers Stem primers can occasionally allow displacement primers not to be used at all, though it is not clear why this is so. This has a major implication for primer design, as it allows the ability to omit one displacement primer or even both, if necessary.

qPCR

In some embodiments, an in vitro nucleic acid amplification assay for use in the methods of the present disclosure is qPCR. Real-time quantitative polymerase chain reaction (qPCR) determines, the fractional cycle number ($C_t$) at which the well's rising fluorescence (proportional to product formation) crosses a set threshold that is several standard deviations above the baseline fluorescence (Higuchi, et al., (1993) Kinetic PGR analysis: real-time monitoring of DNA amplification reactions, *Biotechnology* (NY), 11: 1026-1030, which is incorporated by reference in its entirety). The $C_t$ versus log (amount of input target DNA) plot is linear, allowing relative quantitation of unknowns by comparison to a standard curve derived from amplifying, in the same plate, serial dilutions of a reference DNA sample.

In some embodiments, a qPCR assay is normalized, for example, a signal from a target sequence can be normalized to a signal from a reference sequence. In some embodiments, a target sequence and reference sequence are measured in separate (monoplex) reactions. In some embodiments, a reaction includes a dye that fluoresces upon intercalation into any double-stranded DNA, e.g., ethidium bromide or SYBR Green I, etc. In some embodiments, a target sequence and reference sequence are measured in the same reaction vessel via a multicolor multiplex qPCR. In some embodiments, a multiplex qPCR uses separate fluorescent dyes with distinct excitation/emission spectra for each of the DNA sequences being quantified (Wittwer, et al., (2001) Real-time multiplex PCR assays. *Methods,* 25, 430-442, which is incorporated by reference in its entirety).

Kits

In some embodiments, the present disclosure provides kits comprising materials useful for amplification and detection and/or sequencing of *Cannabis* plant nucleic acid (e.g., DNA). In some embodiments, *Cannabis* plant nucleic acid sample includes detection of all or part of a THCA synthase gene sequence and/or a CBDA synthase gene sequence as described herein. In some embodiments, a kit in accordance of the present disclosure is portable.

Suitable amplification reaction reagents that can be included in an inventive kit include, for example, one or more of: buffers; enzymes having polymerase activity; enzyme cofactors such as magnesium or manganese; salts; nicotinamide adenide dinuclease (NAD); and deoxynucleoside triphosphates (dNTPs) such as, for example, deoxyadenosine triphospate; deoxyguanosine triphosphate, deoxycytidine triphosphate and deoxythymidine triphosphate, biotinylated dNTPs, suitable for carrying out the amplification reactions.

In some embodiments, a kit comprises 1, 2, 3, 4, 5, 6, 7, 8, 9, 10, 11, 12, 13, 14, 15, 16, 17, 18, 19, 20, or more primer sequences for in vitro nucleic acid amplification. Primer sequences may be suitable for in vitro nucleic acid amplification with any of the methods described herein (e.g., QT-PCR, LAMP, etc.). In some embodiments, a kit of the present disclosure includes reagents suitable to perform a colorimetric LAMP assay for amplification of one or more *Cannabis* gene sequences as described herein.

Depending on the procedure, a kit may further include one or more of: wash buffers and/or reagents, hybridization buffers and/or reagents, labeling buffers and/or reagents, and detection means. The buffers and/or reagents included in a kit are preferably optimized for the particular amplification/detection technique for which a kit is intended. Protocols for using these buffers and reagents for performing different steps of the procedure may also be included in a kit.

In some embodiments, a kit may further include one or more reagents for preparation of nucleic acid from a plant sample. For example, a kit may further include one or more of a lysis buffer, a DNA preparation solution (e.g., a solution for extraction and/or purification of DNA). Kits may also contain reagents for the isolation of nucleic acids from biological specimen prior to amplification. Protocols for using these reagents for performing different steps of the procedure may also be included in a kit.

Furthermore, kits may be provided with an internal control as a check on the amplification procedure and to prevent occurrence of false negative test results due to failures in the amplification procedure. An optimal control sequence is selected in such a way that it will not compete with the target nucleic acid sequence in the amplification reaction (as described above).

In some embodiments, a kit may further include reagents for an amplification assay to characterize the gender of a *Cannabis* plant.

Reagents may be supplied in a solid (e.g., lyophilized) or liquid form. Kits of the present disclosure may optionally comprise different containers (e.g., vial, ampoule, test tube, flask or bottle) for each individual buffer and/or reagent. In some embodiments, each component will generally be suitable as aliquoted in its respective container or provided in a concentrated form. Other containers suitable for conducting certain steps of inventive amplification/detection assay(s) may also be provided. Individual containers of a kit are preferably maintained in close confinement for commercial sale.

A kit may also comprise instructions for using the amplification reaction reagents, primer sets, primer/probe sets according to the present disclosure. Instructions for using a kit according to one or more methods of the present disclosure may comprise instructions for processing the biological sample, extracting nucleic acid molecules, and/or performing one or more amplification reactions; and/or instructions for interpreting results. In some embodiments, a kit may comprise instruction for determining, assessing and/or classifying a *Cannabis* plant used in the described methods as a Type Ia, Type Ib, Type IIa, Type IIb, Type IIc, Type IIIa, Type IIIb, Type IV or Type V plant.

Other features of the invention will become apparent in the course of the following descriptions of exemplary embodiments which are given for illustration of the invention and are not intended to be limiting thereof.

EXEMPLIFICATION

Example 1: Genotyping *Cannabis* Plants

Bt and Bd alleles have been proposed as a model for generating Type I, II, III, and IV plants. While this classification system can be predictive, the exact DNA sequences that govern them remain unknown. Single molecule sequencing was performed to identify mutations in gene sequences in cannabinoid synthesis pathway(s) (e.g., THCA synthase and CBDA synthase). This sequencing revealed a more refined structure of the inheritance and revealed numerous additional subtypes that can be identified by genotyping to predict chemical inheritance. See, FIG. 2. As illustrated in FIG. 2, a *Cannabis* plant may be characterized as a Type Ia, Type Ib, Type IIa, Type IIb, Type IIc, Type IIIa, Type IIIb, Type IV or Type V plant.

Example 2: Assay for Genotyping THCA Synthase

This example describes development of superior isothermal nucleic acid amplification assays for detection of THCA synthase. Specifically, a colorimetric LAMP assay for detection of THCA synthase is described. It is envisioned that such a colorimetric LAMP assay may be portable, so that can it be performed at a point of grow to resolve *Cannabis* chemotypes in a rapid and scalable manner.

Challenges with genotyping a THCA synthase include, for example, (1) that there are many pseudogene sequence copies of THCA synthase and (2) that THCA synthase gene sequences are highly polymorphic. For at least this reason, designing primers can be difficult and testing such primers on a few samples does not provide adequate population diversity to guarantee assay performance in the broader markets. The present disclosure addresses these deficiencies with a novel Long Range (2130 bp) LAMP assay that includes a primer that anneals to a promoter region of THCA synthase and internal primers that are less prone to effects resulting from polymorphisms.

Weiblen, Stagginus and Onofri suggested primers for THCA synthase detection but failed to test enough samples to find fatal polymorphisms in their detection approach (Weiblen et al., (2015), *The New Phytologist*, PMID: 26189495; Staginnus et al., (2014) *Journal of Forensic Sciences*, 59(4):919-26, PMID: 24579739; and Onofri et al., (2015), supra, each of which is incorporated by reference in its entirety). While Kitamura et al. described a portable LAMP assay for THCA synthase, the assay was performed using only two THCA+ cultivars and one fiber type. Consequently, Kitamura et al. did not consider the full complexity of *cannabis* genotypes in circulation. Moreover, the primers used in Kitamura's assay annealed to different regions in a THCA synthase gene sequence. As a result, and shown herein, the present disclosure recognizes that the Kitamura primers were insufficient for detecting/amplifying a THCA synthase gene sequence in numerous common *Cannabis* cultivars. In fact, sequence analysis of the Kitamura primers revealed that the 5' end of the Kitamura BIP primer sits on a common I63E and I63F polymorphisms described by Onofri et al., (2015), supra, which is incorporated by reference in its entirety. As this 5' end becomes the 3' end in the second strain synthesis of a LAMP reaction, presence of this polymorphism could impair or stall the LAMP reaction. A similar problem existed with other Kitamura primers, which traversed the P333R variant and the Glu265Gln variants described by Onofri, et al., (2015), supra, incorporated by reference in its entirety.

Amplification issues resulting from polymorphisms in an underlying gene sequence is a common problem with genetic studies of THCA synthase gene sequences. THCA synthase gene sequences are under selective breeding pressure and has a 4-fold higher polymorphism rate than the rest of the genome. There is a SNP approximately every 25 nucleotides in THCA synthase gene sequences, making primer design internal to a THCA synthase gene sequence complicated. To address this, primers (e.g., F3 and B3 primers for LAMP) were designed that were external to a THCA synthase gene sequence, where there is more sequence conservation. This results in a THCA synthase gene sequence amplicon of greater than 2000 nucleotides. There was no expectation that such a reaction would work, as there were no reports of Long Range LAMP assays in the literature and the common design tools found at Primer Explorer did not allow primer design of targets this large.

Materials and Methods

LAMP assay 10 ul 2×LAMP mix (NEB Catalog #M1800S)
2 ul of primer cocktail
6 ul ddH20 (pH 6.5)
2 ul DNA (4 mm leaf biopsy boil in 100 ul ddH20, 5% Chelex)
Exemplary THCA synthase Long Range LAMP primers are provided in FIG. 9 and Table 2:

TABLE 2

| | | |
|---|---|---|
| THC_BIP | CACACAAGCACGTATTTGGGCTTTAGTTTTCACCTTAACTAACCT | SEQ ID NO: 8 |
| THC_FIP | GACTCGCATGATTAGTTTTTCCTATCCTTATGTGTCCCAAAATCC | SEQ ID NO: 9 |
| THC_Loop1 | TCCCTATAATTGAGATACGCCAAT | SEQ ID NO: 10 |
| THC-F3 | ATGGGAACCATAATAAACTATAAAAGTCATT | SEQ ID NO: 11 |
| THC_B3 | TATGATTGTCTACACAGTTCTAATGTAGATTTTC | SEQ 1D NO: 12 |

To compare efficacy of Kitamura primers ("K primers") to exemplary Long Range primers ("LR primers"), LAMP assays were performed with these primers on various strains of *Cannabis* plants. Results are shown in FIG. 5, panel (A). In FIG. 5, panel (A), the text on the left side of the image indicates the strain of *Cannabis* plant for each row of samples that was tested by LAMP amplification. The top row included samples from Granddaddy Purple (GDP), the second row from the top included samples from Otto, the third row from the top included samples from a first hemp strain, the fourth row from the top included samples from a second hemp strain, the fifth row from the top included samples from Grape Stomper (RSP10516), and the bottom row included samples from Erk Train X Deadhead OG (RSP10517). A sample obtained from each strain was placed in the first and third columns. For each strain, a LAMP assay using the K primers was performed in the first column, and a LAMP assay using the LR primers was performed in the third column.

As shown in FIG. 5, panel (A), the two hemp strains displayed a negative result for THCA synthase using either the K primers or the LR primers. As a hemp strain would be expected to be THCA$^+$/THCA$^-$, this result showed that LAMP amplification using either the K primers or the LR primers was not giving a false positive result. The Otto strain, which expresses THCA synthase, displayed a positive result using the K primers, which showed that LAMP amplification using the K primers detected the presence of a THCA synthase gene. However, the GDP strain of *Cannabis* plant, which also expresses THCA synthase, had a negative result when LAMP amplification was performed with K primers, while giving a positive result when LAMP amplification was performed with LR primers. This results showed that LR primers are able to successfully detect a THCA gene sequence by LAMP amplification, and do so in strains for which K primers are unable to detect a THCA gene sequence by LAMP amplification.

To determine how a Long Range LAMP assay of THCA synthase would perform at various temperatures, LAMP assays with LR primers were performed on various samples over a range of temperatures (temperatures indicated on right side of FIG. 5, panel (B)). As indicated in FIG. 5, panel (B), the first two columns of samples were obtained from THCA synthase negative hemp strains. The third column included samples from a THCA synthase positive *Cannabis* strain. The fourth column included samples from a Granddaddy purple strain. The eighth column included a negative control, and the ninth column included a positive control. Amplification of the THCA synthase gene sequence was successful for the THCA synthase positive *Cannabis* strain, the Granddaddy Purple strain, and the positive control at each of the temperatures tested. These data showed that LAMP assays using LR primers were able to properly detect THCA synthase positive strains across a broad temperature profile.

The exemplary Long Range LAMP assay of THCA synthase was repeated on various different *Cannabis* strains that are known to be THCA synthase positive. See, FIG. 6. FIG. 6, depicts LAMP amplifications with LR primers on 28 different known THCA synthase positive strains of *Cannabis* at 65° C., for 50 minutes. Wells H6-H9 were control samples. As can be seen, all 28 THCA synthase positive samples had successful amplification with the exemplary LR primers.

Accordingly, this example demonstrates that LAMP assays using long range primers (such as the exemplified LR primers) of THCA synthase gene sequences was robust and reliable. This example also demonstrates the shortcomings of LAMP amplification using the Kitamura primers for accurately detecting THCA synthase gene sequences in *Cannabis* strains.

Example 3: Combined THCA Synthase/CBDA Synthase Assay

This example describes characterization of the CBDA synthase Bd allele as a four nucleotide deletion within the coding sequence of this gene. This example also describes development of amplification assays for detection of wild-type (CBDA$^{wt}$) and mutant (CBDA$^{Bd}$) CBDA synthase gene sequences.

Kitamura simply assessed presence of a single gene sequence (THCA synthase) and its deleted pseudogene sequence copies in certain hemp fiber varietals. Thus, the LAMP assay described in Kitamura (at best) only differentiated Type I or II *Cannabis* from other types (Type II-V), but failed to refine certain chemotype categories. To more rigorously stratify the numerous classes of cannabinoid production other gene sequence(s) that compete for the same cannabinoid precursor (e.g., cannabigerolic acid or CBGA) should be considered. Since both THCA synthase and CBDA synthase compete for cannabigerolic acid, the mutational spectrum of both of these gene sequences with respect to one another was examined.

Figure 4:
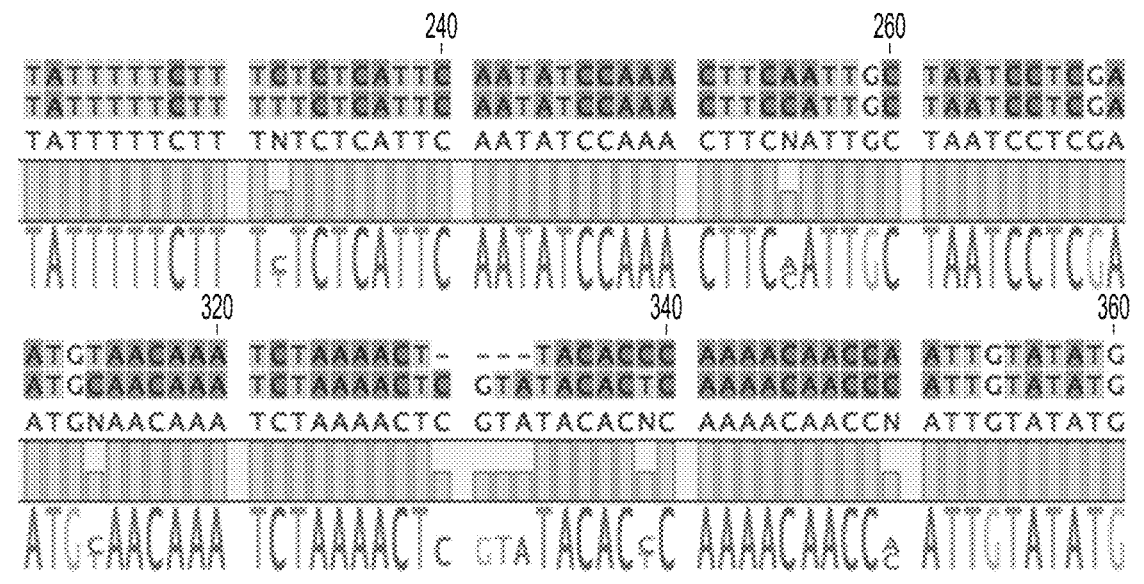

To characterize CBDA synthase, single molecule sequencing of CBDA synthase in dozens of *Cannabis* cultivars was performed. This sequencing revealed a 4 nucleotide frame shifting deletion that governs the Bd allele. The Bd allele was then surveyed in more than 50 hemp and CBD lines to confirm the Bd allele and its phenotype. A consensus sequence for the region of the CBDA synthase gene sequence that includes this deletion is shown in FIG. 4.

Figure 7:
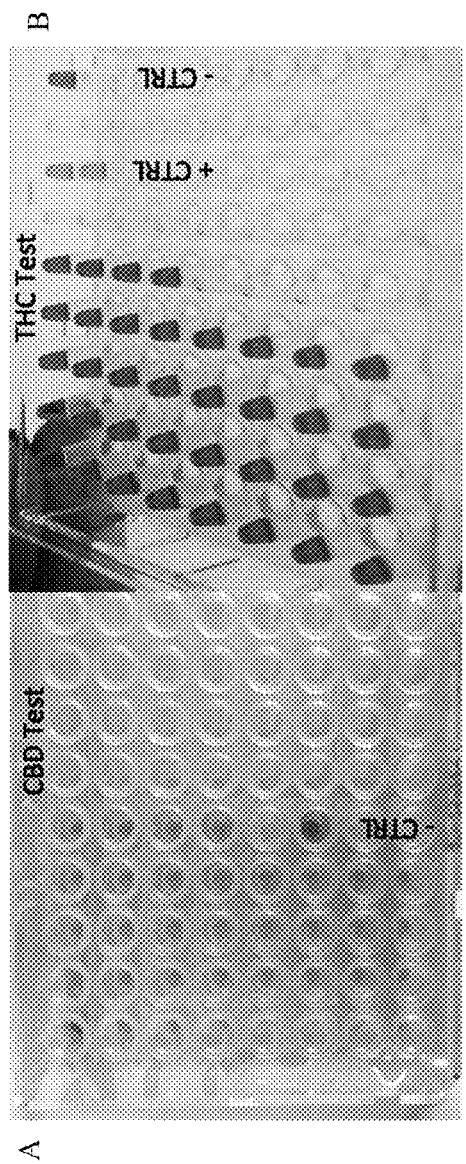
FIG. 7: depicts isothermic (LAMP) amplification of (Panel (A)) a CBDA synthase gene sequence and (Panel (B)) isothermic (LAMP) amplification of THCA gene sequence on various hemp varietals of *Cannabis*. Panel (C) includes a map of the samples run in both Panels (A) and (B).

Assays that targeted a 4 nucleotide deletion in the CBDA synthase gene sequence (4bpDel) (See, FIG. 4, residues 330-333) were designed. Various different hemp lines that were known to be THCA synthase negative were tested by both an exemplary CBDA synthase assay and an exemplary LAMP assay using LR primers for a THCA synthase gene sequence. FIG. 7 shows LAMP assays for amplification of wild-type CBDA synthase gene sequence (panel (A)) and THCA synthase gene sequence (panel (B)) on 38 different hemp strains (i.e., THCA synthase negative strains). A plate map describing the hemp strain in each well is provided at the bottom (panel (C). As shown in FIG. 7, panel (A), all samples but one (sample M2 in well A1) resulted in amplification of a wild-type CBDA synthase gene sequence. Further, as shown in FIG. 7, panel (B), LAMP assay using LR primers for a THCA synthase gene sequence consistently showed no amplification on hemp samples. These results showed that the chemotype of *Cannabis* strains were accurately detected by performance of a CBDA synthase assay and an LAMP amplification using LR primers for a THCA synthase gene sequence.

For the one hemp sample (A1) that failed to amplify in the exemplary CBDA synthase gene sequence assay, when this sample was repeated using a different DNA purification method, amplification of CBDA synthase gene sequence was observed. Thus, it was concluded that the result for this particular sample was a false negative that resulted from other experimental conditions.

With two assays, discernment of THCA synthase positive plants from CBDA synthase positive plants was achieved. The copy number of THCA synthase or CBDA synthase in the genome of *Cannabis* plants could not be detected, however. Copy number can be useful information for breeders looking to breed plants that produce high levels of THC or CBD. In order to assess copy number, a deletion in the CBDA synthase gene sequence was targeted.

Exemplary CBDA$^{wt}$ synthase primers (which hybridize to a wild-type CBDA synthase gene sequence) are provided in FIG. 9 and Table 3:

TABLE 3

| CBD_BIP | CAATCTTAGATTCACCTCTGACACAAGACATGTGAAGGAGTGAC | SEQ ID NO: 13 |
|---|---|---|
| CBD_FIP | TGTATTGTCGAATTTAGGACAGACAATGCAACAAATCTAAAACTCGTA | SEQ ID NO: 14 |
| CBD_Loop1 | CAATGGGTTGTTTTGAGTGT | SEQ ID NO: 15 |

TABLE 3-continued

| CBD_Loop2 | ACCCCAAAACCACTTGT | SEQ ID NO: 16 |
| CBD_F3 | CTTCTCGCAATATATTCCCAAT | SEQ ID NO: 17 |
| CBD_F3_v2 | ATGCTTCTCGCAATATATTCCCA | SEQ ID NO: 27 |
| CBD_B3 | GCATAGAATAGTGCCTTGGAT | SEQ ID NO: 18 |

Exemplary CBDA$^{del}$ synthase primers (which hybridize to a mutant CBDA synthase gene sequence including a 4 nucleotide deletion) are provided in FIG. 9 and Table 4:

TABLE 4

| CBD_BIP | CAATCTTAGATTCACCTCTGACACAAGACATGTGAAGGAGTGAC | SEQ ID NO: 13 |
| CBD-NEG_FIP | TGTATTGTCGAATTTAGGACAGACAATGCAACAAATCTAAAACTTACA | SEQ ID NO: 19 |
| CBD_Loop1 | CAATGGGTTGTTTTGAGTGT | SEQ ID NO: 15 |
| CBD_Loop2 | ACCCCAAAACCACTTGT | SEQ ID NO: 16 |
| CBD_F3 | CTTCTCGCAATATATTCCCAAT | SEQ ID NO: 17 |
| CBD_F3_v2 | ATGCTTCTCGCAATATATTCCCA | SEQ ID NO: 27 |
| CBD_B3 | GCATAGAATAGTGCCTTGGAT | SEQ ID NO: 18 |

The present disclosure encompasses a recognition that detection of both wild-type and mutant CBDA gene sequences will enable genetic differentiation of strains, for example, to differentiate a CBDA$^-$/CBDA$^+$ genotype from a CBDA$^+$/CBDA$^+$ genotype.

Figure 8:
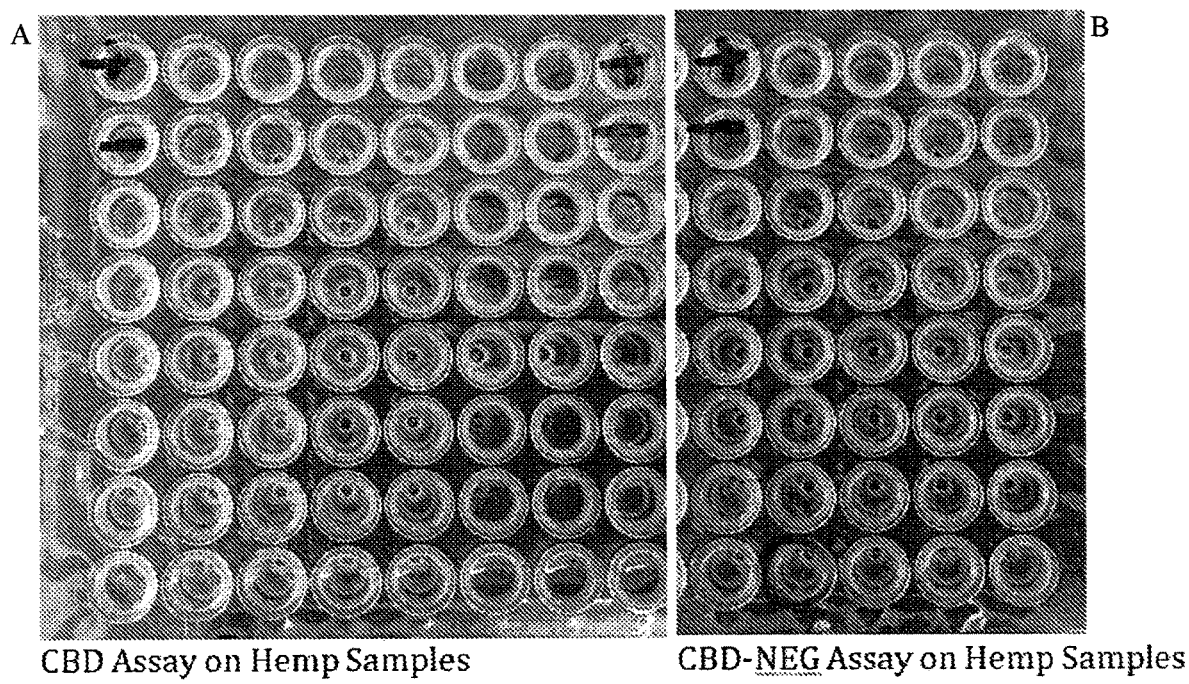
FIG. 8: depicts isothermic (LAMP) amplification assays for CBDA$^{wt}$ (Panel (A)) and CBDA$^{del}$ (Panel (B)) sequences on various hemp varietals of *Cannabis*.

FIG. 8 depicts results obtained from exemplary LAMP assays for amplification of CBDA$^{wt}$ and CBDA$^{del}$ (e.g., CBDA$^{Bd}$) gene sequences. FIG. 8, panel (A), depicts results obtained from LAMP assays with CBDA$^{wt}$ primers on various hemp samples. Most of the samples resulted in amplification of a CBDA$^{wt}$ gene sequence. FIG. 8, panel (B), depicts results from LAMP assays with CBDA$^{del}$ primers on various hemp samples. As can be seen, most of these samples did not amplify a CBDA$^{del}$ gene sequence.

The present disclosure encompasses a recognition that detection of both wild-type and mutant THCA gene sequences will enable genetic differentiation of strains. In order to assess THCA synthase copy number, one or more sequence variants can be targeted. For example, primers can be used that target the *Cannabis* THCA synthase A411V variant.

Thus, combined THCA synthase/CBDA synthase assays provided herein can differentiate additional types of *Cannabis* plants. In some embodiments, methods in the context of the present disclosure can differentiate Type I, Type II, Type III, Type IV, and Type V plants. As described herein, the present disclosure further provides new sub-classification of plants we term Type Ia, Type Ib, Type IIa, Type IIb, Type IIc, Type IIIa, Type IIIb, Type IV and Type V *Cannabis* plants, see, e.g., FIG. 2 and Table 1 (above).

EQUIVALENTS

Those skilled in the art will recognize, or be able to ascertain using no more than routine experimentation, many equivalents to the specific embodiments of an invention described herein. The scope of an invention described is not intended to be limited to the above Description, but rather is as set forth in the following claims:

What is claimed is:

1. A method of detecting whether a tetrahydrocannabinolic acid (THCA) synthase gene sequence is present in a *Cannabis* plant, comprising:
   obtaining a sample collected from the *Cannabis* plant that contains nucleic acids;
   contacting the nucleic acids with at least five primers specific for the THCA synthase gene sequence;
   amplifying the THCA synthase gene sequence when present among the nucleic acids; and
   detecting amplicons upon amplification of the THCA synthase gene sequence, wherein:
   the primers specific for the THCA synthase gene sequence include a primer specific for a promoter sequence of the THCA synthase gene sequence;
   amplification of the THCA synthase gene sequence indicates that the THCA synthase gene sequence is at least 2000 nucleotides long; and
   a colorimetric Loop-Mediated Isothermal Amplification (LAMP) assay is performed.

2. The method of claim 1, wherein the primer specific for the promoter sequence of the THCA synthase gene sequence binds to the promoter sequence at a location that is 200-1000 nucleotides upstream of a THCA synthase open reading frame.

3. The method of claim 1, wherein the THCA synthase gene sequence is between 2100-2200 nucleotides long.

4. The method of claim 1, wherein the *Cannabis* plant is a *C. sativa, C. indica,* or *C. ruderalis* plant.

5. The method of claim 1, wherein the *Cannabis* plant is characterized as a Type Ia, Type Ib, Type IIa, Type IIb, Type IIc, Type IIIa, Type IIIb, Type IV, or Type V plant.

6. The method of claim 1, wherein the primers specific for the THCA synthase gene sequence include two primers comprising sequences that are at least 90% identical to SEQ ID NO: 11 and SEQ ID NO: 12, respectively.

7. The method of claim 1, wherein the primers specific for the THCA synthase gene sequence include six primers comprising sequences that are at least 80% identical to each of SEQ ID NOS: 8-12.

8. The method of claim 1, wherein the primers specific for the THCA synthase gene sequence include six primers comprising sequences that are at least 90% identical to each of SEQ ID NOS: 8-12.

9. The method of claim 1, wherein the primers specific for the THCA synthase gene sequence include a primer comprising a sequence complementary to 20-60 nucleotides of SEQ ID NO: 6 and/or a primer comprising a sequence complementary to 20-60 nucleotides of SEQ ID NO: 7.

10. The method of claim 1, wherein the primers specific for the THCA synthase gene sequence comprise at least one primer comprising a sequence that is at least 70% identical to any of SEQ ID NOS: 8-12.

11. The method of claim 1, wherein the primers specific for the THCA synthase gene sequence comprise at least one primer comprising a sequence that is at least 80% identical to any of SEQ ID NOS: 8-12.

12. The method of claim 1, wherein the primers specific for the THCA synthase gene sequence comprise at least one primer comprising a sequence that is at least 80% identical to SEQ ID NO: 11 or SEQ ID NO: 12.

13. The method of claim 1, wherein the primers specific for the THCA synthase gene sequence comprise at least one primer comprising a sequence that is at least 90% identical to any of SEQ ID NOS: 8-12.

14. A method of detecting whether a tetrahydrocannabinolic acid (THCA) synthase gene sequence is present in a *Cannabis* plant, comprising:
   obtaining a sample collected from the *Cannabis* plant that contains nucleic acids;
   contacting the nucleic acids with at least five primers specific for the THCA synthase gene sequence;
   amplifying the THCA synthase gene sequence when present among the nucleic acids; and
   detecting amplicons upon amplification of the THCA synthase gene sequence, wherein:
   the primers specific for the THCA synthase gene sequence include a primer specific for a promoter sequence of the THCA synthase gene sequence;
   the primer specific for the promoter sequence of the THCA synthase gene sequence binds to the promoter sequence at a location that is 200-1000 nucleotides upstream of a THCA synthase open reading frame; and
   a colorimetric Loop-Mediated Isothermal Amplification (LAMP) assay is performed.

15. The method of claim 14, wherein the primers specific for the THCA synthase gene sequence further include a primer that binds to a sequence that is 50-1000 nucleotides downstream of the THCA synthase open reading frame.

16. The method of claim 15, wherein the THCA synthase gene sequence is at least 2000 nucleotides long.

17. The method of claim 15, wherein the THCA synthase gene sequence is between 2100-2200 nucleotides long.

18. A method of detecting whether a tetrahydrocannabinolic acid (THCA) synthase gene sequence is present in a *Cannabis* plant, comprising:
   obtaining a sample collected from the *Cannabis* plant that contains nucleic acids;
   contacting the nucleic acids with at least five primers specific for the THCA synthase gene sequence;
   amplifying the THCA synthase gene sequence when present among the nucleic acids; and
   detecting amplicons upon amplification of the THCA synthase gene sequence, wherein:
   the primers specific for the THCA synthase gene sequence include a primer specific for a promoter sequence of the THCA synthase gene sequence;
   the amplicons of the THCA synthase gene sequence include at least part of the THCA synthase promoter and 5' UTR; and
   a colorimetric Loop-Mediated Isothermal Amplification (LAMP) assay is performed.

19. The method of claim 18, wherein the THCA synthase gene sequence is at least 2000 nucleotides long.

20. The method of claim 18, wherein the THCA synthase gene sequence is between 2100-2200 nucleotides long.

* * * * *